(12) United States Patent
Lafanechere et al.

(10) Patent No.: US 8,604,048 B2
(45) Date of Patent: Dec. 10, 2013

(54) PYRIDOCARBAZOLE TYPE COMPOUNDS AND APPLICATIONS THEREOF

(75) Inventors: Laurence Lafanechere, Grenoble (FR); Emilie Vassal, Crolles (FR); Caroline Barette, Grenoble (FR); ChiHung Nguyen, Antony (FR); Christian Rivalle, Paris (FR); Renaud Prudent, Saint-Egreve (FR)

(73) Assignees: Centre National de la Recherche Scientifique, Paris (FR); Institut Curie, Paris (FR); Commissariat a l'Energie Atomique et aux Energies Alternatives, Paris (FR); Universite Paris Sud (Paris XI), Orsay (FR)

( * ) Notice: Subject to any disclaimer, the term of this patent is extended or adjusted under 35 U.S.C. 154(b) by 0 days.

(21) Appl. No.: 13/202,426

(22) PCT Filed: Feb. 19, 2010

(86) PCT No.: PCT/IB2010/000538
§ 371 (c)(1),
(2), (4) Date: Oct. 26, 2011

(87) PCT Pub. No.: WO2010/095042
PCT Pub. Date: Aug. 26, 2010

(65) Prior Publication Data
US 2012/0041017 A1 Feb. 16, 2012

(30) Foreign Application Priority Data
Feb. 20, 2009 (FR) .................................... 09 00786

(51) Int. Cl.
*A61K 31/437* (2006.01)
*C07D 471/04* (2006.01)
*C40B 30/04* (2006.01)

(52) U.S. Cl.
USPC .................................. 514/285; 546/70; 506/9

(58) Field of Classification Search
None
See application file for complete search history.

(56) References Cited

U.S. PATENT DOCUMENTS

| 4,434,290 A | 2/1984 | Bisagni et al. |
| 4,966,971 A | 10/1990 | Bisagni et al. |
| 2007/0054905 A1 | 3/2007 | Tazi et al. |

FOREIGN PATENT DOCUMENTS

| EP | 0 010 029 | 4/1980 |
| EP | 0 317 416 | 5/1989 |
| FR | 2 859 474 | 3/2005 |

OTHER PUBLICATIONS

Richard B. Silverman, The Organic Chemistry of Drug Design and Drug Action, Chapter 2: Drug Discovery, Design, and Development, Academic Press, p. 5-51 (1992).*
Bisagni, E., et al., "Synthesis of 1-Substituted Ellipticines by a New Route to Pyrido[4,3-*b*]-carbazoles," Journal of the Chemical Society, J.C.S. Perkin I, pp. 1706-1711, (1979) XP 009122515.
Dormoy, J.-R., et al., "Synthese Industrielle En Serie; Ellipticine. II," Tetrahedron, vol. 49. No. 14, pp. 2915-2938, (1993), (with English Abstract) XP 002545386.
Rivalle, C., et al., "Antitumor amino-substituted pyrido[3',4':4,5]pyrrolo[2,3-g]isoquinolines and pyrido[4,3-b]carbazole derivatives: synthesis and evaluation of compounds resulting from new side chain and heterocycle modifications," Journal of Medicinal Chemistry, vol. 26, No. 2, pp. 181-185, (1983) XP 002163117.
Gribble, G.W., "Chaper 7—Synthesis and Antitumor Activity of Ellipticine Alkaloids and Related Compounds," The Alkaloids, vol. 39, pp. 239-352, (1990) XP 009122574.
International Search Report issued Oct. 29, 2010 in PCT/IB10/00538 filed Feb. 19, 2010.

* cited by examiner

*Primary Examiner* — Janet L Andres
*Assistant Examiner* — Timothy R Rozof
(74) *Attorney, Agent, or Firm* — Oblon, Spivak, McClelland, Maier & Neustadt, L.L.P.

(57) ABSTRACT

Pyridocarbazole-type compounds of formula (I):

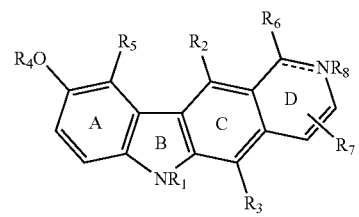

are provided as a medicament, and more particularly for application in anticancer chemotherapy. Also provided is a pharmaceutical composition with the compound and methods for preventing and/or treating neurodegenerative-type pathologies, such as Alzheimer's disease and schizophrenia, parasitoses, such as malaria, or glaucomas.

16 Claims, 17 Drawing Sheets

PYRIDOCARBAZOLE TYPE COMPOUNDS AND APPLICATIONS THEREOF

The present invention relates to the use of pyridocarbazole type compounds as a medicament, and more particularly to the application thereof in anticancer chemotherapy and also for the treatment of other types of diseases (psychiatric, viral, parasitic or fungal diseases); these compounds correspond to the formula (I), the structural archetype of which may be compared to that of ellipticine; the present invention also relates to specific compounds of formula (I), and also to pharmaceutical compositions comprising the compounds of formula (I).

The mitotic spindle has long been identified as an important target in anticancer chemotherapy, given the crucial role that it plays in cell division. Impairment of the function of the microtubules may have drastic effects on the viability of the cells causing an arrest of the cell cycle and possibly even inducing cell apoptosis.

Microtubules form, with the actin microfilaments and the intermediate filaments, the cytoskeleton of the eukaryotic cells. These are hollow tubular aggregates constituted of a single dimeric protein, i.e. the tubulin. In mammalian cells, the microtubule networks are in general nucleated at an organizing centre: the centrosome. These networks carry out multiple and vital roles such as organization of the cytoplasm, positioning of the organelles, cell motility and cell division. During mitosis, the microtubule network is reorganized to form the mitotic spindle, which is machinery used by cell to separate the duplicated chromosomes into two identical sets, before its cleavage into two daughter cells. Mitotic spindle integrity is controlled by specific checkpoints. Any undetected mitotic spindle dysfunction could be at the origin of genomic instability and thus represents a potential source of tumorigenesis (Castillo et al., 2007; Kops et al., 2005).

Microtubules assemble by polymerization of $\alpha,\beta$-dimers of tubulin. Microtubules are highly dynamic polymers able to rapidly polymerize from free tubulin dimers and to depolymerise just as rapidly. Microtubule dynamics are crucial to mitosis (Jordan and Wilson, 2004; Niethammer et al., 2007).

The microtubule dynamic behaviour network is tightly controlled in cells. It is regulated by a balance between activities of microtubules-stabilizing and microtubules destabilizing proteins that comprise, depending of the cell types, a family of the so-called microtubule associated proteins (MAP) STOP proteins, tau proteins, survivin, stathmin/Op18, Tog, and the microtubule depolymerising kinesins, MCAK and Kif2A. Moreover, the interaction of microtubule growing tips with some proteins, such as CLIP 170, results in microtubule stabilization. All these seemingly unrelated proteins have in common that they bind the tubulin dimer, either along the microtubule lattice or at the microtubule ends. The binding of these proteins to tubulin is tightly regulated, by phosphorylation/dephosphorylation processes or by tubulin post-translational modifications, such as the tubulin tyrosination cycle (FIG. 1), for example (Barra et al., 1998; Lafanechére and Job, 2000; MacRae, 1997; Peris et al., 2006; Peris et al., 2009). This latter modification involves the cyclic removal of the carboxy-terminal tyrosine residue of the α-tubulin chain by an un-characterized tubulin carboxypeptidase (TCP) and the re-addition of a tyrosine residue at the same location by tubulin tyrosine ligase (TTL). It has recently been shown that tubulin tyrosination regulates microtubule interactions with CAP-Gly microtubule plus end tracking proteins, such as CLIP-170 (Peris et al., 2006).

TTL, the enzyme that catalyses the tubulin tyrosination reaction, adds tyrosine to soluble, detyrosinated tubulin and does not react efficiently with tubulin once it is assembled into microtubules. Less is known about TCP mainly because it has not yet been purified to homogeneity. Indirect evidence indicates that TCP is likely to prefer polymerized substrate and that it binding to microtubules may be required for its function. TOP acts slowly on microtubules while TTL recharges Glu-tubulin quickly upon release from microtubules (FIG. 1) (MacRae, 1997).

As a consequence of the substrate specificity of TTL and the kinetics differences of TTL and TOP, tyrosinated tubulin (Tyr-tubulin) is the main component of dynamic microtubules, being the dominant tubulin variant in cycling cells in vitro, whereas Glu-tubulin is a marker of long-lived stable microtubules (Gundersen et al., 1984; Gundersen et al., 1987; Wheland and Weber, 1987). Depending on the cell type, these detyrosinated microtubules are either not detectable or represent a small subpopulation of the cellular. Detyrosinated microtubules accumulate when microtubules are stabilized by effector proteins or drugs, such as paclitaxel (Fonrose et al., 2007; Vassal et al., 2006).

Several anticancer drugs clinically important, including the Vinca alkaloids, vinblastine, vincristine, and vinorelbine and the taxanes paclitaxel and docetaxel specifically target tubulin and modify microtubules dynamics. Considering the clinical success of these agents, tubulin represents one of the most highly validated cancer targets identified to date.

Furthermore, in addition to cancer, the involvement of the microtubule cytoskeleton in the etiology of a large number of diseases has been described, such as for example mental disorders (Andrieux et al., 2006; Andrieux et al., 2002; Begou et al., 2008) and neurodegenerative diseases (Dermaut et al., 2005; Garcia et Cleveland, 2001), and viral (Ruthel et al., 2005), bacterial (Margalit et al., 2004) and parasitic (Morrissette and Sibley, 2002) infections. The pharmacological agents targeting the microtubule cytoskeleton and its various effectors may therefore exhibit a therapeutic advantage for the treatment of a large number of diseases (Lafanechére, 2008).

Thus, the treatments used in anticancer chemotherapy target, in a favoured manner, the dynamic behaviour of the microtubules. In particular, it may be blocked by many agents that can bind to different sites of tubulin. Structural data concerning the binding of these different agents on tubulin have now been obtained. Zinc-induced sheets of paclitaxel-stabilized tubulin protofilaments have been used for construction of a model of tubulin with bound paclitaxel. After fitting this model into electron density microtubule maps, the authors concluded that paclitaxel binds to β-tubulin facing the microtubule lumen (Snyder et al., 2001). The X-ray structure of vinblastine bound to tubulin in a complex with the protein stathmin has shown that the vinblastine introduces a wedge at the interface of two tubulin molecules and thus interferes with tubulin assembly (Gigant et al., 2005).

These studies have led to the characterization, to date, of three binding sites of poisons of microtubules on tubulin: the domain of periwinkle alkaloids located at the interface between two α/β-tubulin dimers, the site of taxoids located on the β subunit and that of colchicine located at the interface between the α subunit and the β subunit.

These various agents are classified according to whether they destabilize or stabilize the microtubules:

Agents that destabilize the microtubules:

Periwinkle alkaloids, capable of depolymerizing the microtubules, have been identified as agents capable of arresting the cells in mitosis, with aberrant mitotic spindles. Subsequently, vincristine and vinblastine were introduced into clinical medicine in the 1960s and are still widely used in chemotherapy for testicular cancer, Hodgkin's disease or acute lymphoid leukemia.

Mention may also be made of colchicine or combretastatin, which inhibit the polymerization of the microtubules and also nocodazole.

Agents that stabilize the microtubules:

Taxanes, and more particularly paclitaxel, interact specifically and reversibly with the microtubules with a stoichiometry of about one mole of taxane per one mole of tubulin. This interaction is accompanied by a stabilization of the microtubules which then become resistant to a depolymerization induced in vitro, by cold temperature (4° C.), or by the presence of $Ca^{2+}$ ions.

Paclitaxel and the other taxanes are differentiated from other anti-tubulin poisons mainly by the stabilizing effect that they exert on the microtubules. Cancer drugs such as paclitaxel or Vinca alkaloids were previously thought to work through opposite mechanisms. There are now known to act by modifying microtubule dynamics, and not through increasing or decreasing the overall microtubule mass. Despite their antitumour efficacy, especially in breast cancer, ovarian cancer and lung cancer, taxanes are extremely toxic since they also act on the microtubules of non-cancerous cells in proliferation (hematopoietic cells, mucous cells, etc.). Finally, they may adversely affect the peripheral neurons and give rise to significant side-effects.

Other natural products that exhibit microtubule-stabilizing properties such as epothilones and discodermolide, are currently being studied in clinical trials in humans for their antitumour properties.

The therapeutic success of paclitaxel has maintained the advantage for the search for therapeutic agents that target tubulin. Considering the clinical success of these agents, tubulin is today one of the best validated targets in anticancer chemotherapy (Giannakakou et al., 2000; Jackson et al., 2007; Zhou and Giannakakou, 2005).

However, although mostly valuable, the substances known from the prior art are not ideal. They have several side-effects, principally myelosuppression and peripheral neurotoxicity. Neurotoxic side-effects related to tubulin drugs are not surprising because tubulin is a major player not only in cell division but also in mitosis-independent cytoskeletal functions. Moreover, many cancers are inherently resistant to these drugs or become so during prolonged treatment. This is often the result of multidrug resistance caused by overexpression of P-glycoprotein, which functions as a drug efflux pump or other drug efflux pumps such as breast cancer resistant protein, BCRP. Other sources of resistance include increased expression of tubulin isotypes to which a particular drug binds less effectively and alterations in tubulin structure, by post-translational modification or mutation, which reduces binding.

Several strategies have been proposed for the development of potentially more effective and less toxic drugs. One is to improve existing drugs or to find new ones that target tubulin.

Another approach consists in to target other proteins, only expressed in dividing cells such mitotic checkpoint proteins, with inhibition also leading to mitotic arrest. Members of different protein families (kinases and kinesins) are currently under investigation. Because many of these proteins are thought to have very specialized and specific functions at discrete phases mitoses, it was assumed that inhibition of these proteins could potentially allow an improved therapeutic index relative to the existing anti-mitotic therapy that target tubulin. However the rationale underlying the search of specific inhibitors of mitotic spindle function—with potentially less side-effects—instead of new tubulin agents, is getting weaker. On the one hand, kinases such as Aurora A, known for its specific action in mitosis, have recently been shown to exert an effect on the interphase microtubule skeleton. On the other hand, because some of the anti-tumor effect of microtubule poisons might also be attributed to interphase interaction with the tubulin cytoskeleton (Pan and Snell, 2007; Pugacheva at al., 2007).

The search for agents that disrupt the microtubule dynamics, directly targeting tubulin (or microtubules) or targeting proteins capable of regulating microtubule dynamics (Bhat and Setaluri, 2007; Muller et al., 2007), remains an important issue in cancerology.

The Applicant has surprisingly found that the compounds of formula (I) according to the present invention have several advantages compared to the compounds known from the prior art:

they are capable of generating Glu-tubulin and of inducing a resistance of the microtubule network to a depolymerization induced by nocodazole. In vitro, they do not act directly on tubulin. They therefore stabilize the microtubules but have a mode of action that is different from that of other known microtubule-stabilizing compounds, that are capable of attaching to tubulin, such as taxanes or epothilones;

they are significantly less toxic than the compounds known from the prior art, and are active even in cases of high resistance observed with the compounds of the prior art;

they have, moreover, an effect on the actin cytoskeleton. The latter is reorganized and becomes to some extent more resistant to a depolymerization induced by latrunculin. The cell motility is inhibited. Thus, by inhibiting the cell motility, these compounds can reduce the remote dissemination of tumours; they thus have additional anti-metastatic properties;

they thus constitute advantageous alternative treatments, especially when the appearance of a resistance to other treatments (taxanes) is for example observed.

One subject of the present invention is therefore the compounds of formula (I) as a medicament.

Thus, the first subject of the present invention relates to tetracylic compounds that correspond to the formula (I) below:

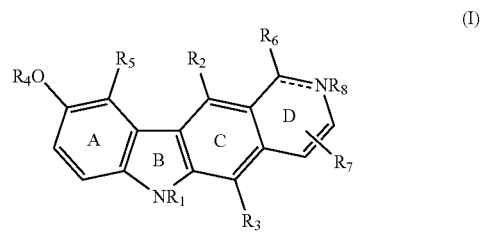

in which:

$R_1$ represents a hydrogen atom, an alkyl radical having 1 to 4 carbon atoms, an aminoalkyl group having 1 to 4 carbon atoms, or a monoalkylaminoalkyl or dialkylaminoalkyl group in which the two alkyl radicals have 1 to 4 carbon atoms;

$R_2$ represents a hydrogen atom or an alkyl radical having 1 to 4 carbon atoms;

$R_3$ represents an alkyl radical having 1 to 4 carbon atoms;

—$OR_4$ represents a hydroxyl radical, an alkoxy radical having 1 to 4 carbon atoms or an alkoxy radical of formula —O—$(CH_2)_n$—Z, or an ester radical having 1 to 4 carbon atoms or an ester radical of formula —OC(O)Z, in which:

Z is a cycloalkyl group having 3 to 6 carbon atoms, or an aryl group, chosen from phenyl, benzyl, pyridyl, pyrimidyl, triazyl and oxazolyl groups, said aryl group possibly being optionally substituted at the ortho, meta or para position by one, two or three substituents, which are identical or different, chosen from halogen atoms, —OH, —$NO_2$ or —$NH_2$ groups, alkyl radicals having 1 to 4 carbon atoms, alkoxy radicals having 1 to 4 carbon atoms and monoalkylamino or dialkylamino radicals having 1 to 4 carbon atoms; and n is an integer ranging from 1 to 4, and preferably equal to 1;

or an —$OR_4$ radical corresponding to the formula:

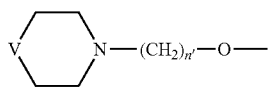

in which:

V is chosen from $CH_2$, O, NH or N-alkyl, the alkyl group having 1 to 4 carbon atoms; and n' is equal to 2 or 3;

$R_5$ represents a hydrogen atom or a dialkylamino-methyl group in which the alkyl radical has 1 to 4 carbon atoms;

$R_6$ represents an oxygen atom bound to the ring D by a double bond, a halogen atom, or an alkoxy radical having 1 to 4 carbon atoms;

$R_7$ represents a hydrogen atom or an alkyl radical having 1 to 4 carbon atoms;

$R_8$ represents a hydrogen atom, an alkyl radical, a hydroxyalkyl radical, an alkylcarboxyalkylene radical of formula

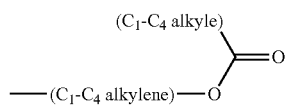

or a dialkylphosphatealkylene radical of formula

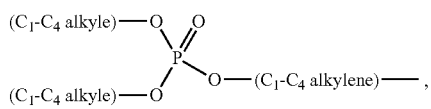

in which the alkyl and alkylene radicals have 1 to 4 carbon atoms, or an ester radical having 1 to 4 carbon atoms, and $R_8$ being present only when $R_6$ is an oxygen atom bound to the D ring by a double bond;

and their pharmaceutically acceptable salts, as a medicament.

Some compounds of formula (I) as defined above have already been described in the prior art as intermediate products, but never as medicaments (J. C. S. Perkin I, 1979, 7, 1706-1711; Tetrahedron, 1993, 49(4), 2915-2938; J. Med. Chem., 1983, 26, 181-185; Patent Applications EP 0 317 416 A and EP 0 010 029 A).

The compounds of formula (I) may be represented by the following structures:

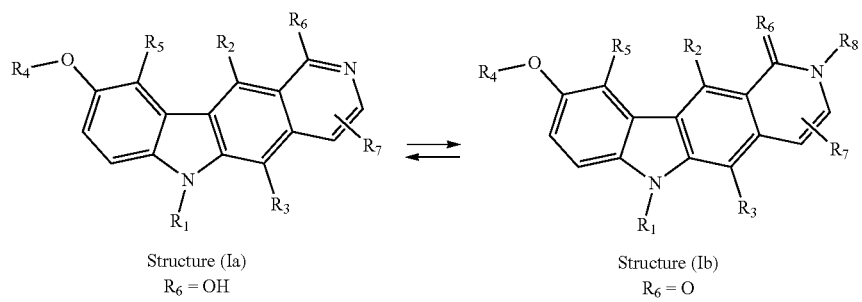

Structure (Ia)
$R_6$ = OH

Structure (Ib)
$R_6$ = O

The compound of formula (I) of the invention may also be in the form of a salt. In this case, it is preferably a salt of hydrochloric acid, of hydrobromic acid, of maleic acid or of methanesulphonic acid.

Among the advantageous applications of said compounds, mention may be made of the treatment of cancers, the treatment of metastases, and also the treatment of other types of diseases, such as psychiatric, viral, parasitic and fungal diseases.

Surprisingly, the compounds of formula (I), as defined above, are able to penetrate into cells and to stabilize the microtubules and the microfilaments giving rise to the formation of Glu-tubulin, a slowing down of the dynamic behaviour of microtubules, a reorganization and a stabilization (as indicated by some resistance to latrunculin-induced depolymerisation) of actin microfilaments. These compounds have a mode of action that is different from that of other known microtubule-stabilizing compounds such as taxanes or epothilones, or of that of known compounds for stabilizing actin filaments such as jasplakinolide.

More specifically, the compounds according to the invention induce a reorganization of actin filaments conjugated to an inhibition of cell motility, and the Inventors have now found that LIMK1 may be a target of the compounds of formula (I).

The structural archetype of the compounds according to the invention is similar to that of ellipticine, a purified alkaloid isolated from *Ochrosia elliptica* and corresponding to the following formula:

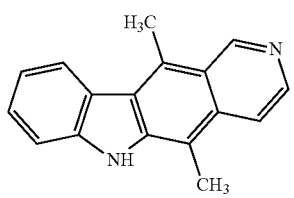 [SMILES: Cc1c2ccncc2c(C)c2c1[nH]c1ccccc12]

Ellipticine and ellipticin derivatives are known for their anticancer and cytotoxic activity in certain cancers (Dodion et al., 1982; Hayat et al., 1974; Juret et al., 1980; Le Mee et al., 1998; Paoletti et al., 1980; Tura et al., 1984); their mode of action relies mainly on its properties of DNA intercalation, topoisomerase II inhibition and formation of covalent adducts with DNA, via P450 cytochromes and peroxidases. Unlike the compounds according to the invention, ellipticine does not have any effect on the stabilization of cell microtubules, nor on that of actin microfilaments.

Many derivatives or analogues of ellipticine have been described:

International PCT application WO 2007/135538 describes the use of ellipticium derivatives (9-hydroxyellipticine) for the treatment of metastatic cancers or cancers which cannot be treated by conventional cytotoxic chemotherapies. The compounds described induce a remodelling of the cytoskeleton of actin in the tumour cells, involving a reduction in the cell mobility and the recovery of the property of cell adhesion.

European application EP 0 209 511 describes chloride hydrochlorides of 2-aminoalkyl-9-hydroxyellipticinium derivatives of formula:

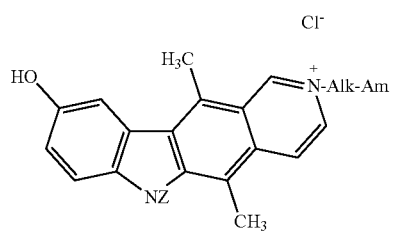

where -Alk represents a lower alkylene group, and -Am represents a di(lower alkyl)amino group, these compounds possibly being used as an active principle in a pharmaceutical composition having an antitumour action.

French Application FR 2 859 474 describes indole-derived compounds and the use of such compounds for the preparation of a medicament that can be used to treat diseases related to the process of splicing pre-messenger RNAs in the cell, and more particularly for treating genetic diseases in which the splicing of pre-messenger RNAs is altered, such as certain cancers in which the global splicing process is affected (breast cancer, colon cancer and certain lymphomas).

The compounds according to the invention, the structures of which are different from those of the compounds described in these various documents, surprisingly have microtubule-stabilizing properties; they also have properties of reorganizing the actin network and to stabilize it to some extent and act mainly as LIMK1 inhibitors.

LIMK1 (LIM kinase 1) regulates actin polymerization by phosphorylating the actin depolymerization factor, cofilin; LIMK1 is also involved in the regulation of microtubule disassembly and the microtubule (MT) destabilization, by phosphorylating protein p25. Thus, LIMK1 coordinates both microtubules disassembly and actin polymerization (Gorovoy et al., 2005; Acevedo et al., 2007).

More precisely, LIMK1, a serine/threonine kinase containing LIM and PDZ domains plays, therefore, a central role in the regulation of the actin cytoskeleton by phosphorylating cofilin on serine 3 and inactivating its actin-severing activity (Arber at al., 1998; Yang et al., 1998). Given the importance of the actin cytoskeleton, LIMK1 plays a central role in numerous biological processes, particularly in the regulation of cell morphology and motility.

During progression of tumour cells to a metastatic phenotype, they undergo a series of changes that begin with loss of contact inhibition and increased motility, allowing them to migrate from the primary tumour site, invade distant organs and induce neo-vascularization resulting in metastasis (Yoshioka et al., 2003).

As tumour cells become metastatic, the normal mechanisms that control the actin cytoskeleton, cell shape and motility may be subverted so as to promote invasiveness. Considering the role of LIMK1 in phosphorylation of cofilin, it plays a central and critical role in tumour invasion and metastasis. It has been proposed that the balance between phosphorylated and non-phosphorylated cofilin determines the metastatic potential of tumour cells. Indeed, LIMK1 has been found to be overexpressed in malignant melanoma cells, breast cancer tumours, in prostate tumours and in tumour cell lines, where increased phosphorylated cofilin was also observed (Scott and Olson, 2007; Wang at al., 2007)

The compounds according to the invention are thus toxic to various cancer lines ($IC_{50}$ of the order of 1 to 60 μM depending on the lines and the compounds), especially to lines that have developed resistance mechanisms to the drugs used in anticancer chemotherapy (taxanes, Vinca alkaloids, antracyclines, etc.).

The compounds according to the invention therefore represent a novel class of anticancer agents, particularly useful for cancers that are resistant to current chemotherapies and in metastases.

The compounds of the invention acting as LIMK1 inhibitors may also be used in other conditions involving LIMK1, such as neurodegenerative diseases (Bernard, 2007; Heredia et al., 2006), primary pulmonary hypertension (Scott and Olson, 2007) and glaucoma.

Advantageously, the $R_1$ radical is a hydrogen atom. However, the $R_1$ radical may also be a dialkylaminoalkyl group of formula —$(CH_2)_{n''}$NR'R", in which:

R' and R", which are identical or different, represent a hydrogen atom or an alkyl radical having 1 to 4 carbon atoms, and n" varies from 1 to 4.

Preferably, the compound of formula (I) corresponds to a structure in which the radical $R_2$ is a hydrogen atom or a methyl radical, and more preferably still a methyl radical.

As regards the $R_3$ radical, the latter is preferably a methyl radical.

The —$OR_4$ radical may advantageously be an —OH group or a methoxy radical.

When the —$OR_4$ radical is an alkoxy radical of formula —O—$(CH_2)_n$—Z or an ester radical of formula —OC(O)Z, said —$OR_4$ radical is preferably a benzyl ether radical of formula —O—$CH_2$—$C_6H_5$, or an ester radical of formula —OC(O)$C_6H_5$, the latter possibly being optionally substituted at the ortho, meta or para positions by a substituent chosen from —$NO_2$, —$NH_2$, —$N(CH_3)_2$, —CN, —$CH_2NH_2$ or —$CH_2N(CH_3)_2$ groups.

The alkoxy radicals of formula —O—(CH$_2$)$_n$—Z and ester of formula —OC(O)Z, as defined above, are the radicals —OR$_4$ which are the most preferred.

The R$_5$ radical may advantageously be a hydrogen atom or, when the R$_5$ radical is a dialkylaminoalkyl group, dimethylaminomethyl.

Preferably, the R$_8$ radical of the compound of formula (I) is a hydrogen atom.

The R$_6$ radical is preferably an oxygen atom bound to the ring D by a double bond or a halogen atom, and more preferably still an oxygen atom bound to the ring D by a double bond.

According to one preferred embodiment, the R$_6$ radical represents an oxygen atom bound to the ring D by a double bond, and the R$_8$ radical represents a hydrogen atom, the bond between the carbon atom bearing the radical R$_6$ and the nitrogen atom bearing the radical R$_8$ being in this case a single bond. In this case, the compounds of formula (I) according to the invention correspond to the structure (Ib) below:

Structure (Ib)

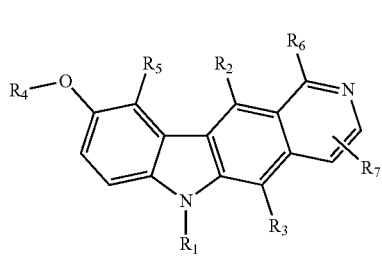

Among the compounds of formula (I), seems that compounds of structure (Ib) are the most active as LIMK1 inhibitors, and preferably among said compounds of structure (Ib), those in which:

—OR$_4$ represents a hydroxyl radical, a radical of formula —O—(CH$_2$)$_n$—Z, or a radical of formula —OC(O)Z, as defined above, R$_1$ is a hydrogen atom, and R$_8$ is a hydrogen atom, are particularly preferred.

According to another variant, the R$_6$ radical represents a halogen atom, and more preferably a chlorine atom, or an alkoxy radical having 1 to 4 carbon atoms.

In this case, the compounds of formula (I) according to the invention correspond to the structure (Ia) below:

Structure (Ia)

In the most preferred embodiments, the compound of formula (I) corresponds to the formula:

Compound 1

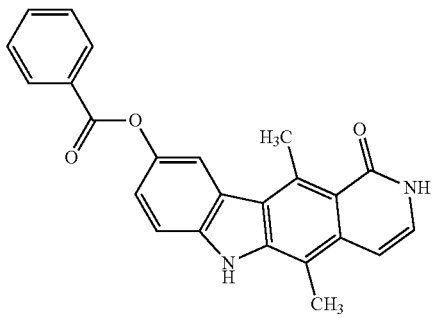

or to the formula:

Compound 3

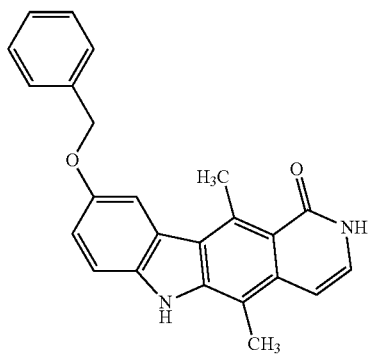

or to the formula:

Compound 4

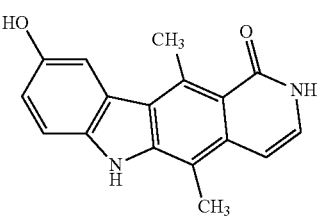

or to the formula:

Compound 9

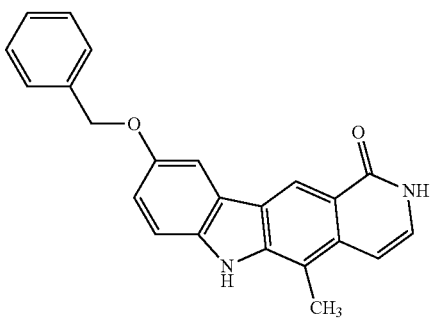

or to the formula:

Compound 11

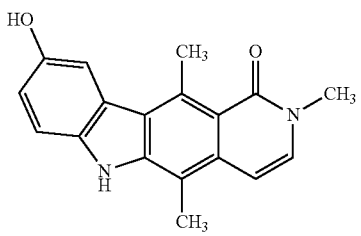 [SMILES: Cc1c2ccn(C)c(=O)c2c(C)c2c1[nH]c1ccc(O)cc12]

Another subject of the present invention is the specific compounds of formula (I) below:

Compound 7

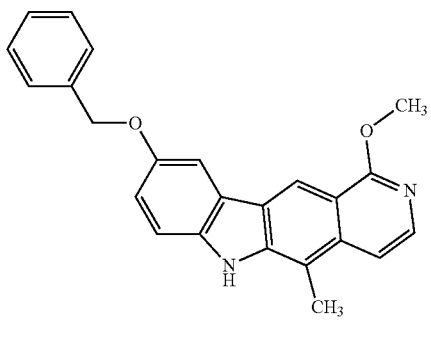

Compound 10

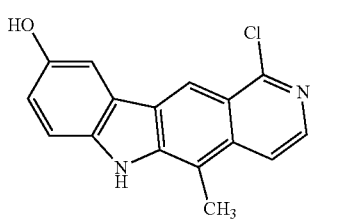

Another subject of the present invention is a pharmaceutical composition comprising, as the active principle, at least one compound as defined above and at least one pharmaceutically acceptable vehicle.

According to one advantageous embodiment of said pharmaceutical composition, it also comprises another anticancer active principle.

Said pharmaceutical compositions include both compositions in solid form (tablets, gel capsules, capsules, etc.) and compositions in liquid form (solutions, suspensions or emulsions) and include the excipients suitable for oral, topical or parenteral administration.

The administration of the compounds or compositions according to the invention is preferably carried out via an oral route or via a parenteral route (perfusion or IV injection, in particular). Administration by perfusion over a suitable period, generally between 2 h and 24 h, and preferably between 2 h and 12 h is generally preferred.

The doses of compounds vary depending on the formulation selected, the method of administration and the tumour to be treated. Other factors such as age, weight, height or sex and also certain biological parameters (excretion rate, association with other medicaments, allergies, etc.) must also be taken into account. The examples below enable a person skilled in the art to determine the most suitable doses.

Another subject of the present invention is a method of evaluating the microtubule-stabilizing activity of a compound of formula (I), as defined above.

A screening test has been the subject of a publication in J. Biomol. Screen (Vassal et al., 2006); however, it has been adapted in order to evaluate compounds of formula (I). Thus, said method comprises:

1. after incubating eukaryotic cells with the compound to be tested, permeabilization of the cells with a buffer which protects the microtubule network but allows the elimination of the depolymerized tubulin;

2. after fixation of the cells, the Tyr-tubulin is labelled with an anti-tyrosinated tubulin primary antibody and a secondary antibody which emits at a wavelength $\lambda 1$, [for example in the red region (Cyanine 3)] the Glu-tubulin is labelled with an anti-detyrosinated tubulin primary antibody and a secondary antibody which emits at a wavelength $\lambda 2$ [for example, in the green region (Alexa Fluor® 488)], followed by the quantification of the fluorescence at the various wavelengths, especially using a simple reader, with the aim to identify the dynamic microtubules most sensitive to the depolymerizing agents and the stabilized microtubules;

3. a supplementary labelling of the nuclei (Hoechst), in order to evaluate the state of the cell layer;

4. incubation of the compound to be tested with HeLa cells under the same conditions as step 1 and elimination of the compound 1f a fluorescence is observed at the wavelength $\lambda 2$ (for example at the same wavelength as the Alexa Fluor® 488 antibody); this makes it possible to eliminate false positives via an immunofluorescence analysis of the microtubule network by visualizing the actual effect of the compound to be evaluated on the microtubules; indeed, a green labelling of aggregates, which persists even after washing the cells, is not specific to the microtubules;

5. an analysis of the effects on the location and the shape of the mitochondria by comparing the effect of sodium azide and of the compound to be tested on the mitochondria, and exclusion of the compound to be tested if it exhibits a mode of action similar to the sodium azide by labelling with a mitochondrial marker, such as chloromethyl-X-rosamine (NitoTracker® marker), which has the property of passively diffusing through the mitochondrial membrane and of accumulating in active mitochondria.

It is known that sodium azide is capable to induce the generation of stabilized microtubules, thus generating Glu-tubulin (De Brabander et al., 1982; Gundersen et al., 1987). Sodium azide is an inhibitor of mitochondrial respiration. The explanation for this phenomenon would be that, by blocking electron transport during oxidative phosphorylation, this substance gives rise to ATP depletion. This will block an unidentified step of depolymerization of the microtubules and give rise to an increase of Glu-microtubules in the cell;

6. a step of analysis of the effect of the compound to be tested on the dynamics of the microtubule network. For this, HeLa cells are incubated for 2 h with the compound to be tested, then optionally treated with 10 µM nocodazole for 30 minutes. The possible protective effect of the compound to be tested with respect to a depolymerization induced by the nocodazole is then revealed by an analysis of the immunofluorescence labelling of the microtubule network and a quantification using a microplate reader or microscopic analysis;

7. a step of analysis of the effect of the compound to be tested on the actin network, via incubation of HeLa cells with the compound to be tested. This incubation step is optionally prolonged by a step of co-incubation with a depolymerizing agent of the actin network, latrunculin B. Finally, a labelling of F-actin with a phallotoxin coupled to a fluorophore (emission at λ2, for example, Alexa Fluor® 488). When the actin network is stabilized, the latrunculin-induced depolymerization of the actin network is limited.

Actin, just like tubulin, forms networks. These networks mechanically support the plasma membrane, thus determining its shape and its plasticity, and enable the cell to migrate, to endocytose particles and to divide. It is known that the actin network and the microtubule network, even if there are specific substances targeting for each of these networks, are closely inter-regulated. Therefore, certain molecules that act on the microtubules may also have an effect on the actin network (Baudouin et al., 2008; Enomoto, 1996; Mogilner and Keren, 2009).

Finally, another subject of the present invention is the compounds of formula (I) for use as medicaments, in particular:

for preventing and/or treating neurodegenerative-type pathologies, and more particularly for preventing and/or treating Alzheimer's disease and schizophrenia;

for preventing and/or treating parasitoses, and more particularly for preventing and/or treating malaria;

for preventing and/or treating glaucomas.

Another application could also be the use of the compounds of formula (I) as pesticides.

The invention also relates to an in vitro method for screening molecules susceptible to inhibit or stabilize the activity of LIMK1 comprising:

(i) contacting LIMK1 with a compound of Formula (I) according to the invention, optionally labelled;

(ii) adding the compound to be tested, and (iii) evaluating the displacement of compound of formula (I) by the compound to be tested.

In the case where compound of formula (I) is not labelled, the evaluation of step (iii) is performed by HPLC or a similar method.

In the case where compound of formula (I) is labelled (fluorophore, radiolabelled isotope, biotinylation or similar labelling method), the evaluation of step (iii) is performed on an appropriate solid support (microplates, for instance) and the label is measured on said solid support; a decrease of the label showing that the compound to be tested is a competitor of compound of formula (I) and is therefore a LIMK1 inhibitor.

The invention also relates to an in vivo method for screening direct or indirect LIMK1 activators or phosphatase inhibitors, comprising:

(i) contacting a compound of formula (I) with an eukaryotic cell, preferably a human cell, (ii) evaluating the inhibitor effect of said compound of formula (I) by measuring the decrease of phosphorylation of a LIMK1 substrate, for example cofilin, (iii) adding the compound to be tested, and (iv) measuring the effect of the compound to be tested on the inhibition of the LIMK1 substrate phosphorylation.

Steps (ii) and (iii) may be performed separately or simultaneously.

Step (iv) consists of measuring the level of phosphorylation of the LIMK1 substrate and comparing it to the measure obtained at step (ii).

If phosphorylation is restored or increased, the compound to be tested is a direct or indirect activator of LIMK1 or a phosphatase inhibitor.

Besides the preceding arrangements, the invention also comprises other arrangements which will emerge from the remainder of the description which follows, which relates to examples that highlight the stabilizing properties of tetracyclic compounds of formula (I) according to the invention, and also to the appended drawings in which:

FIG. 1 corresponds to the detyrosination/tyrosination cycle of tubulin;

FIG. 2 represents the depolymerizing effect of nocodazole on the microtubules of HeLa cells;

FIG. 3 represents the effect of the Compound 1 of the invention on the stability of microtubules at low temperature. The HeLa cells are incubated with paclitaxel or without, with the Compound 1 of the invention, for 2 h, then exposed for 30 minutes at 4° C. The amount of tubulin in the cells treated with the Compound 1 of the invention is measured with a microplate reader, then reported as a percentage of the amount of tubulin measured in the wells containing the cells treated with paclitaxel (100%);

FIG. 4 represents the effect of nocodazole on the microtubules of the HeLa cells treated with the Compound 1 of the invention. The HeLa cells are incubated with paclitaxel or without, with the Compound 1 of the invention for 2 h, then exposed for 30 minutes to nocodazole. The amount of tubulin in the cells treated with the Compound 1 of the invention is measured with a microplate reader, then reported as a percentage of the amount of tubulin measured in the wells containing the cells treated with paclitaxel;

FIG. 5 compares the effects of the Compound 1 of the invention with the effect of paclitaxel (Taxol®) on the assembly of the tubulin purified in vitro. Purified tubulin (1 mg/ml) is incubated in PEM buffer in the presence of GTP (1 mM), $MgCl_2$ (5 mM), DAPI (10 µM) at 37° C. The effect of Compound 1 of the invention at various concentrations (×25 µM, ⊙ 50 µM and Δ 100 µM) is compared to that of paclitaxel (Taxol®) (■) and of DMSO (□);

EXAMPLE 1

Characterization of the Products

Figure 1:
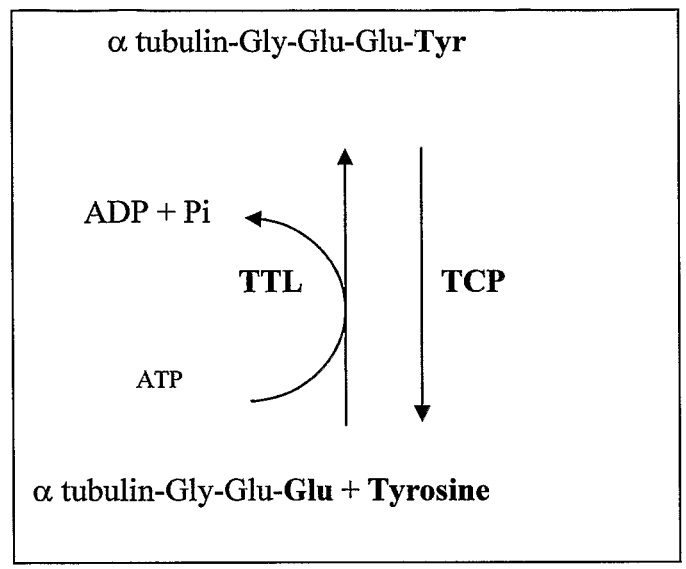

Silica Column Chromatography:

Silica column chromatography is carried out.

It is carried out on a silica gel having a thickness of 0.040-0.063 μm (Merck), previously put into suspension in a given solvent/eluent (the amount of silica having to be equal to 10 to 100 times the amount of crude reaction mixture to be purified). The mixture of products to be separated is adsorbed onto a minimum amount of silica gel, or dissolved in a minimum of solvent, delicately deposited at the top of the column, then chromatographed using a suitable eluent.

Compounds 1 to 6 and 9 to 11 from Table I were synthesized and evaluated.

TABLE I

| Compound | Formula | Stability of the microtubules | Stability of the actin network |
|---|---|---|---|
| 1 | | +++ | +++ |
| 2 | | +/− | − |
| 3 | | +++ | +++ |
| 4 | | ++ | ++ |

TABLE I-continued

| Compound | Formula | Stability of the microtubules | Stability of the actin network |
|---|---|---|---|
| 5 | (structure) | +/− | − |
| 6 | (structure) | ++ | + |
| 9 | (structure) | ++ | ++ |
| 10 | (structure) | ++ | − |
| 11 | (structure) | ++ | ++ |

The Compounds 1 to 6 and 9 have been described in the literature as synthesis intermediates.

Synthesis of Compound 1: 9-benzoyloxy-5,11-dimethyl-2H,6H-pyrido[4,3-b]carbazol-1-one Synthesis as described and published in J. Med. Chem., 1983, 26, 181.

Synthesis of Compound 2: 9-methoxy-5,11-dimethyl-2H,6H-pyrido[4,3-b]carbazol-1-one Synthesis as described and published in J. Chem. Soc. Perkin Trans. 1, 1979, 1706, and Tetrahedron, 1993, 2915.

Synthesis of Compound 3: 9-benzyloxy-5,11-dimethyl-2H,6H-pyrido[4,3-b]carbazol-1-one Synthesis as described and published in J. Chem. Soc. Perkin Trans. 1, 1979, 1706.

Synthesis of Compound 4: 9-hydroxy-5,11-dimethyl-2H,6H-pyrido[4,3-b]carbazol-1-one Synthesis as described and published in J. Med. Chem., 1983, 26, 181.

Synthesis of Compound 5: 1-chloro-9-methoxy-5,11-dimethyl-6H-pyrido[4,3-b]carbazole Synthesis as described and published in J. Chem. Soc. Perkin Trans. 1, 1979, 1706, and Tetrahedron, 1993, 2915.

Synthesis of Compound 6: 1-chloro-9-methoxy-5-methyl-6H-pyrido[4,3-b]carbazole

Synthesis as described and published in J. Chem. Soc. Perkin Trans. 1, 1979, 1706.

Synthesis of Compound 7: 9-benzyloxy-1-methoxy-5-methyl-6H-pyrido[4,3-b]carbazole Compound 7

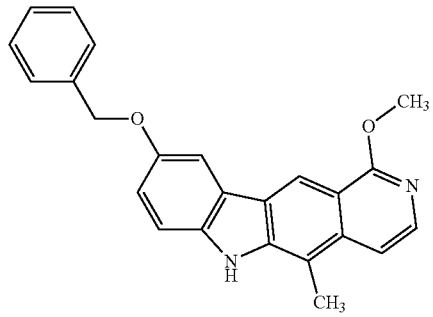

A solution of benzyl bromide (230 μl, 1.9 mMol) in acetone (6 ml) is added at room temperature, over 15 minutes, to a mixture containing 1-chloro-9-hydroxy-5-methyl-6H-pyrido[4,3-b]carbazole (Compound 10) (490 mg, 1.73 mMol), acetone (7 ml), DMF (2 ml) and $K_2CO_3$ (400 mg). The assembly is left stirring for 24 h, then the solvents are subsequently evaporated under vacuum. Water is then added (30 ml). The assembly is again left stirring for 24 h. The solid form is recovered by filtration, washed with water, then dried at room temperature for 18 h. An inter-mediate, 1-chloro-9-benzyloxy-5-methyl-6H-pyrido[4,3-b]carbazole (330 mg, 51% yield) is obtained, after chromatography through a silica column using dichloromethane/ethyl acetate (from 99%/1% to 95%/5%) as eluent.

The product obtained is identical to that obtained according to the method described in J. Chem. Soc. Perkin Trans. 1, 1979, 1706.

The mixture of 1-chloro-9-benzyloxy-5-methyl-6H-pyrido[4,3-b]carbazole obtained above (320 mg, 0.86 mMol), DMF (7 ml) and sodium methoxide (30% solution in methanol, 10 ml) is heated under reflux for 20 h. The reaction mixture is poured into 60 ml of water, then left stirring for 2 h. The solid formed, recovered by filtration, is washed with water then dried.

280 mg (88% yield) of the expected compound 9-benzyloxy-1-methoxy-5-methyl-6H-pyrido[4,3-b]carbazole (Compound 7) are then obtained, after chromatography through a silica column using dichloromethane/ethyl acetate (from 99.5%/0.5% to 99%/1%) as eluent.

The proton NMR spectrum of Compound 7 is the following:
$CDCl_3$ δ (ppm): 8.87 (s, 1H), 8.00 (d, 1H), 7.88 (br s, 1H), 7.80 (d, 1H), 7.55-7.33 (m, 8H), 5.21 (s, 2H), 4.22 (s, 3H), 2.76 (s, 3H).

Microanalyses:
calculated for $C_{24}H_{20}N_2O$ 1.75 $H_2O$: C, 72.09; H, 5.88; N, 7.01;
found: C, 72.22; H, 5.51; N, 7.18.

Synthesis of Compound 8:
1,9-dimethoxy-5-methyl-6H-pyrido[4,3-b]carbazole

Compound 8

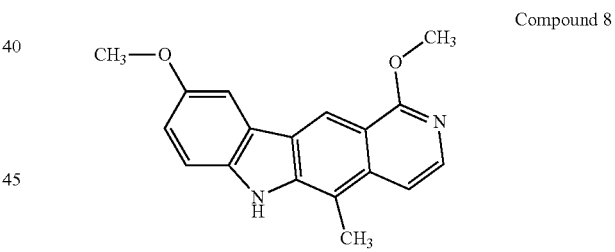

The mixture of 1-chloro-9-methoxy-5-methyl-6H-pyrido[4,3-b]carbazole (prepared according to J. Chem. Soc. Perkin Trans. 1, 1979, 1706) (427 mg, 1.44 mMol), DMF (1.5 ml) and sodium methoxide (30% solution in methanol, 3 ml) is heated under reflux for 24 h. The reaction mixture is then poured into 50 ml of water, then left stirring for 2 h. The solid formed, recovered by filtration, is washed with water then dried.

400 mg (95% yield) of the expected compound 1,9-dimethoxy-5-methyl-6H-pyrido[4,3-b]carbazole (Compound 8) are then obtained, after chromatography through a silica column using dichloromethane/ethanol (from 99%/1% to 98%/2%) as eluent.

The proton NMR spectrum of Compound 8 is the following:
$CDCl_3$ δ (ppm): 8.85 (s, 1H), 7.98 (d, 1H), 7.91 (br s, 1H), 7.68 (d, 1H), 7.41 (d, 1H), 7.35 (d, 1H), 7.11 (dd, 1H), 4.21 (s, 3H), 3.95 (s, 3H), 2.72 (s, 3H).

Microanalyses:
calculated for $C_{18}H_{16}N_2O_2$ 0.5 $H_2O$: C, 71.79; H, 5.65; N, 9.30;
found: C, 71.84; H, 5.49; N, 9.12.

Synthesis of Compound 9: 9-benzyloxy-5-methyl-6H-pyrido[4,3-b]carbazol-1-one Synthesis as described and published in J. Chem. Soc. Perkin Trans. 1, 1979, 1706.

Synthesis of Compound 10: 1-chloro-9-hydroxy-5-methyl-6H-pyrido[4,3-b]carbazole In a 5 ml sealed tube, a mixture of 1-chloro-9-methoxy-5-methyl-6H-pyrido[4,3-b]carbazole (75 mg, 0.25 mMol) (prepared according to J. Chem. Soc. Perkin Trans. 1, 1979, 1706), benzyltriethylammonium chloride (225 mg, 1 mMol) and 37% hydrochloric acid (4 ml) is heated in an oil bath at 140° C. for 24 h.
The reaction mixture is then evaporated, under vacuum, then 20 ml of water are added. The medium is then rendered basic by addition of 28% ammonium hydroxide (0.5 ml), and the solid is recovered by low-temperature filtration, then washed with water and dried using a vacuum desiccator, at a temperature of 200° C. for 18 h.
65 mg (90% yield) of Compound 10 are then obtained, the proton NMR spectrum of which is the following:
DMSO-$d_6$ δ (ppm): 11.30 (s, 1H), 9.21 (s, 1H), 8.87 (s, 1H), 8.16 (d, 1H), 7.98 (d, 1H), 7.71 (d, 1H), 7.40 (d, 1H), 7.07 (dd, 1H), 2.83 (s, 3H).
Microanalyses:
calculated for $C_{16}H_{11}ClN_2O$ 0.25 $H_2O$: C, 66.91; H, 4.04; N, 9.75;
found: C, 66.99; H, 4.26; N, 9.34.

Synthesis of Compound 11: 9-hydroxy-2,5,11-trimethyl-6H-pyrido[4,3-b]carbazol-1-one A mixture of 1-chloro-9-methoxy-5,11-dimethyl-6H-pyrido[4,3-b]carbazole (250 mg, 0.81 mMol) (Compound 5, prepared according to the ref. J. Chem. Soc. Perkin Trans. 1, 1979, 1706, and Tetrahedron, 1993, 2915), acetonitrile (50 ml) and iodomethane (10 ml) is heated at a temperature of 65° C. for 3 h.
The mixture obtained is then evaporated, under vacuum, then 30 ml of 3N sodium hydroxide are added. The mixture is then left stirring for 30 minutes. The brick red solid obtained is recovered by filtration, then washed with water and dried at room temperature for 18 h.
An intermediate is then obtained, 9-methoxy-2,5,11-trimethyl-6H-pyrido[4,3-b]carbazol-1-one, which is used as is, without any other purification.
A mixture comprising the intermediate compound 9-methoxy-2,5,11-trimethyl-6H-pyrido[4,3-b]carbazol-1-one obtained above and pyridine hydrochloride (2 g) is heated under reflux for 30 minutes.
The resulting solution is poured into 60 ml of iced water, and the solid formed is then recovered by low-temperature filtration, washed with two lots of 5 ml of water, then dried using a vacuum desiccator, at a temperature of 20° C. for 18 h.
The solid is then mixed with 20 ml of toluene, then brought to boiling for 5 minutes, before being cooled to 20° C.
130 mg (55% yield) of Compound 11 are then obtained, which is recovered by filtration, washed with 2 lots of 5 ml of toluene, then dried at room temperature for 18 h, the proton NMR spectrum of which is the following:

DMSO-$d_6$ δ (ppm): 11.07 (s, 1H), 9.01 (d, 1H), 7.69 (d, 1H), 7.38 (d, 1H), 7.35 (d, 1H), 6.95 (dd, 1H), 6.68 (d, 1H), 3.45 (s, 3H), 3.39 (s, 3H), 2.59 (s, 3H).
Microanalyses:
calculated for $C_{18}H_{16}N_2O_2$ 1.33 $H_2O$: C, 68.35; H, 5.90; N, 8.86;
found: C, 68.22; H, 5.74; N, 9.27.

Synthesis of Compounds Out of the Invention:
Compound C6: synthesis as described and published in J. Med. Chem., 1980, 181,

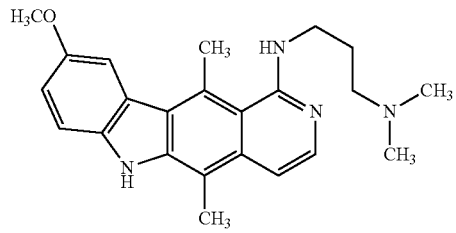

Compound C6

Compound C8: this compound was obtained by refluxing of 9-benzoyloxy-1-chloro-5,11-dimethyl-6H-pyrido[4,3-b]carbazole in N,N-diethylpropane-1,3-diamine in place of N,N-diethylpropane-1,3-diamine as described and published in J. Med. Chem., 1983, 181.

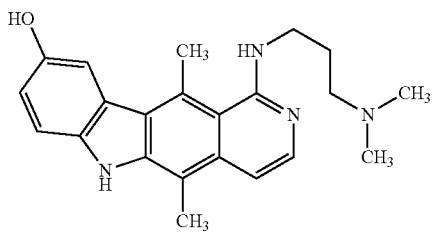

Compound C8

EXAMPLE 2

Materials and Methods

1) Cell Lines

The name, the reference and the origin of the lines are listed in Table II below.

TABLE II

| Name | ATCC reference | Species | Morphology | Origin | Pathology |
| --- | --- | --- | --- | --- | --- |
| HeLa | CCL-2 | Human | epithelial cells | cervix | adenocarcinoma |
| NCI-H460 | HTB-177 | Human | epithelial cells | lung | carcinoma |
| 786-O | CRL-1932 | Human | epithelial cells | kidney | adenocarcinoma |
| MCF-7 | HTB-22 | Human | epithelial cells | breast | adenocarcinoma |
| MES-SA | CRL-1976 | Human | fibroblast | uterus | uterine sarcoma |
| MES-SA DX5 | CRL-1977 | Human | fibroblast | uterus | uterine sarcoma |

2) Primary Antibodies

The primary antibodies used are listed in Table III below:

TABLE III

| Name | Species of origin | Type | Epitope | Dilution Fluorescence | Dilution Western blot |
|---|---|---|---|---|---|
| YL1/2 | rat | Monoclonal | Tyrosinated tubulin Epitope: EGEEF or EGEEY at C-terminal | 1/4000 | 1/50000 |
| L4 | rabbit | Polyclonal | Detyrosinated tubulin Epitope: EGEE at C-terminal | 1/4000 | 1/400000 |
| α 3A2 | Mouse | Monoclonal | α-tubulin Epitope: DMAALE | | 1/20000 |

3) Secondary Antibodies

The secondary antibodies used are the following:

TABLE IV

| Name | Species of origin | Supplier | Dilution Fluorescence | Dilution Western blot |
|---|---|---|---|---|
| Anti-rat Cyanine 3 | goat | Rockland | 1/500 to 1/1000 | |
| Anti-rabbit Alexa Fluor® 488 | goat | Molecular Probes | 1/500 to 1/1000 | |
| Anti-rat HRPo | monkey | Jackson Immunoresearch | | 1/5000 |
| Anti-rabbit HRPo | goat | Biosource | | 1/5000 |

4) Cell Biology

Cell Culture:

All the lines are grown in 15 ml of culture medium in T75 flasks in a humidified incubator at 37° C. and 5% $CO_2$. To maintain the culture, the cells are divided when they reach confluency by dissociating them with a solution of 0.5% trypsine/EDTA (Gibco, Invitrogen) and reseeded at dilutions varying from 1/5 to 1/20. In order to avoid any drift and variations of the cell properties, these lines are used for 20 passages at most except for the MEF line (primary cells) which it is inadvisable to use beyond 6 passages since these cells stop dividing after a certain number of passages.

The HeLa, NCI-H460 and 786-0 lines are grown in RPMI-1640 with GlutaMAXI™ (Gibco, Invitrogen) supplemented with 10% of foetal calf serum (FCS, Hyclone, Thermo Fisher Scientific) and 1% of penicillin/streptomycin (Gibco, Invitrogen).

The MCF-7 lines are grown in EMEM (ATCC) supplemented with 10% FCS, 1% penicillin/streptomycin and 0.1 mg/ml of insulin (Sigma Aldrich).

The MES-SA and MES-SA DX5 lines are grown in McCoy's 5A (ATCC) supplemented with 10% FCS and 1% penicillin/streptomycin for the first passages then in RPMI-1640 supplemented with 10% FCS and 1% penicillin/streptomycin.

Immunofluorescence:

Staining of tubulin (Tyr, Glu) and nuclei:

Cells grown for two days on glass coverslips, were incubated 3 minutes at 37° C. with or without OPT buffer (Pipes 80 mM, EGTA 1 mM, $MgCl$ 1 mM, Triton X-100 0.5% and glycerol 10% pH 6.8), and then fixed in methanol previously maintained at −20° C. for 10 minutes. The cells are then washed with PBS/0.1% Tween® 20 and incubated for 15 minutes minimum at room temperature with the appropriate primary antibodies (cf. the antibodies from Table III) diluted in a solution of PBS/0.3% BSA/0.02% $NaN_3$. The cells are then washed 3 times with PBS/0.1% Tween® 20. They are incubated for 15 minutes at room temperature with a solution of secondary antibodies (cf. the antibodies from Table IV) and of Hoechst at a final concentration of 1 μg/ml, diluted in PBS/0.3% BSA/0.02% $NaN_3$. Finally, the cells are washed 3 times with PBS/0.1% Tween® 20, then dehydrated with pure ethanol and fixed to slides using a Fluorsave™ mounting solution (Calbiochem, Merck).

Staining of Actin:

The cells are grown on glass coverslips and incubated as for the tubulin staining. After elimination of the medium, the cells are washed with warm PBS then fixed, by addition of a solution of PBS/3.7% formaldehyde for 30 minutes at 37° C. The cells are washed with PBS then permeabilized with a solution of PBS/0.2% Triton X100 for 15 minutes at room temperature. After another washing with PBS, the cells are incubated with a solution of PBS/1% BSA for 30 minutes at room temperature. The cells are then incubated with phalloidin (0.165 μM final concentration) labelled with Alexa Fluor® 488 (Molecular Probes, Invitrogen) for 20 minutes at room temperature. The cells are washed a final time with PBS then dehydrated with pure ethanol. Finally, the cells are fixed to slides using a Fluorsave™ mounting solution.

Staining of Mitochondria:

As for tubulin staining, the cells are grown on glass coverslips and incubated at 37° C. with 5% $CO_2$. Three days after seeding, MitoTracker® Red CMXRos (Molecular Probes, Invitrogen) is added to the culture medium in order to reach a final concentration of 250 nM. The cells are then incubated for 30 minutes at 37° C. with 5% $CO_2$. This marker passively diffuses through the plasma membrane and accumulates into the active mitochondria. After elimination of the medium, the cells are washed with warm medium then fixed by addition of a solution of PBS/3.7% formaldehyde for 30 minutes at 37° C. The cells are rinsed with PBS, then can be permeabilized with a solution of PBS/0.2% Triton X100 for 15 minutes at room temperature if other immunofluorescence staining are needed.

5) Microscopy

Fluorescence images were taken using a microscope (Axioskop 50, Zeiss, Oberkochen, Germany) and 100×/1.3 Plan Neofluar objective, a CololSnap ES charge-coupled device camera (Roper Scientific, Trenton, N.J., USA) and Metaview (Universal Imaging Corp.) software, and were processed using Adobe Photoshop.

Alternatively, the slides are read under various fluorescence microscopes or using a confocal microscope.

6) Cell Growth Test

The cell growth tests are carried out in transparent 96-well microplates (Greiner) after having seeded 100 μl/well of a cell solution having $2 \cdot 10^5$ cells/ml to $5 \cdot 10^5$ cells/ml (depending on the cell lines). After incubating for 24 h at 37° C. with 5% $CO_2$, the culture medium is removed and replaced with solutions of the molecule to be tested at various concentrations. The cells are incubated with these molecules for an additional 48 h at 37° C. with 5% $CO_2$. After elimination of the medium, the cells are washed with blank RPMI (Gibco, Invitrogen) then incubated with 3-(4,5-dimethylthiazol-2-yl)-2,5-diphenyltetrazolium bromide or MTT (0.5 mg/ml final concentration) for 4 h at 37° C. with 5% $CO_2$. MTT (Sigma Aldrich)

makes it possible to estimate the viability of the cells by measuring the activity of a mitochondrial enzyme. Indeed, in living cells, mitochondrial dehydrogenases are capable of cleaving the tetrazolium ring, thus leading to the formation of formazan crystals that are insoluble in an aqueous medium. These crystals are dissolved with the addition of a solubilizing solution (isopropanol, 10% Triton X100, 0.1 N HCl). After stirring, the absorbance is measured at 570 nm using the FLUOstar OPTIMA microplate reader.

7) Test Enabling the Detection of Molecules that Stabilize or Destabilize Microtubules in Microplates HeLa cells are seeded in black-bottomed black 96-well microplates (Greiner 655086) by distributing 90 µl per well of a cell solution containing 40 000 cells/ml, and incubated at 37° C. with 5% $CO_2$. 24 h later, the cells are incubated with the molecules to be tested for 2 h at 37° C. with 5% $CO_2$. The cells are then permeabilized with warm OPT buffer for 6 minutes at 37° C. then fixed in methanol for 10 minutes at room temperature. The cells are rinsed twice with PBS/0.1% Tween® 20 and incubated with the primary antibodies YL1/2 and L4 (cf. the antibodies from Table III) diluted to 1/4000 in a solution of PBS/0.3% BSA/0.02% $NaN_3$ overnight at 37° C. The cells are then washed 3 times with PBS/0.1% Tween® 20, then incubated for 1 h at 37° C. with a solution of Hoechst having a final concentration of 1 µg/ml and of anti-rat Cyanine 3 and anti-rabbit Alexa Fluor® 488 secondary antibodies respectively diluted to 1/500 and 1/1000 in PBS/0.3% BSA/ 0.02% $NaN_3$. After 3 washes with PBS/0.1% Tween® 20, PBS/50% glycerol is distributed into each well. The various fluorescence intensities are measured using the FLUOstar OPTIMA reader.

8) Test for the Action on the Actin Cytoskeleton: Protocol for Evaluating, in Cells, the Stability of the Actin Network to a Depolymerization Induced by Latrunculin B 3 days before the experiment, glass coverslips are deposited under sterile conditions in 24-well microplates. In each well, HeLa cells (15 000 cells per well) in the exponential growth phase are seeded in 500 µl of RPMI medium.
Reagents:
Stock Reagents:
PBS (phosphate buffered saline, ref. P4417, Sigma), PBS/1% BSA (bovine serum albumin, Ref. A3059, Sigma), aliquots of 15 ml, stored at −20° C.; PBS/0.2% Triton X100 (Ref. T8787, Sigma); PBS/0.01% Tween® 20 (Ref. P9916, Sigma); PBS/ 0.3% BSA/0.02% $NaN_3$ (Ref. for the $NaN_3$: 6688, Merck), aliquots of 15 ml stored at −20° C. Phalloidin A488, (Ref. A12379, Invitrogen).
L4: rabbit anti-detyrosinated-tubulin polyclonal antibody (cf. Fonrose et al., Cancer Res., 207, 67:3371-3378).
Anti-rabbit antibody coupled to Cyanine 3 (Ref. 111.165.144, Jackson Laboratories).
Hoechst (bisbenzimide H 33258, Ref. B2883, Sigma) 1 mg/ml stock solution in bidistilled $H_2O$.
Fluorsave® mounting liquid (Ref. 345789, Calbiochem).
Ethanol (Ref. 414-587, Carlo Erba).
To be Prepared the Same Day:
Latrunculin B (Ref. L5298, Sigma) 5 µM: 5 µl of 500 µM latrunculin in 500 µl of RPMI.
DMSO (dimethyl sulphoxide, Ref. D5879, Sigma) 0.25%: 2.5 µl of pure DMSO in 1000 µl of RPMI.
Paclitaxel (Ref. T1912, Sigma) 5 µM: 5 µl of 1 mM paclitaxel in 1000 µl of RPMI.
Compounds (25 µl, final concentration) to be tested:
2.5 µl of compound at a concentration of 10 mM (in DMSO) in 1000 µl of RPMI.

PBS/3.7% formaldehyde: 1.2 ml of 37% formaldehyde (Ref. F1635, Sigma)+12 ml of PBS, to be prepared extemporaneously.
Dilute the phalloidin A488 to a concentration of 0.165 µM in PBS/1% BSA.
Dilute, in PBS/0.3% BSA/0.02% $NaN_3$:
L4 primary antibody to 1/4000.
Anti-rabbit Cyanine 3 secondary antibody to 1/1000.
Hoechst to 1/1000 (=1 µg/ml).
Centrifuge these various diluted products for 10 minutes at 15 000 g, in order to eliminate the possible aggregates.
Implementation of the Test:
Add, to each well, the compounds to be tested at a concentration of 25 0.25% DMSO and 5 µM paclitaxel are used as controls. All the conditions are carried out in duplicate.
Incubate for 2 h in a cell incubator (at 37° C., 5% $CO_2$, under a humid atmosphere).
At the end of the 2 h incubation, 10 µl of 5 µM latrunculin are added every two well (final concentration of latrunculin: 0.1 µM).
The incubation is continued for 10 minutes, before fixing the cells and carrying out the immunostaining of the detyrosinated tubulin and the staining of the actin.
Fixation of the Cells and Staining of the Detyrosinated Tubulin and of the Actin Network:
The cells are washed with 500 µl/well of PBS at 37° C. and then fixed by incubation for 30 minutes at 37° C. with PBS/ 3.7% formaldehyde pre-warmed at 37° C. (500
Incubation for 30 minutes at 37° C.
The following steps are carried out at room temperature.
Aspiration of PBS/3.7% formaldehyde.
3 washes with 500 µl/well of PBS.
The coverslips are then recovered using tweezers and deposited on a suitable support.
Permeabilization with PBS/0.2% Triton X100 (100 µl/coverslip).
The coverslips are then washed 3 times with PBS.
Saturation with PBS/1% BSA (100 µl/coverslip) for 30 minutes.
The coverslips are then washed 3 times with PBS.
Incubation with 0.165 µM fluorescent phalloidin A488 (50 µl/coverslip) for 20 minutes.
The coverslips are then washed 3 times with PBS/0.1% Tween.
Incubation with L4 primary antibody diluted to 1/4000 (50 µl/coverslip) for 15 minutes.
The coverslips are then washed 3 times with PBS/0.1% Tween.
Incubation with the anti-rabbit Cyanine 3 fluorescent secondary antibody (1/1000) and with Hoechst (1/1000) (50 µl/coverslip) for 15 minutes.
The coverslips are then washed 3 times with PBS/0.1% Tween.
Dehydration of the preparation by dipping the coverslips into a bath of 100% ethanol.
Coverslips are fixed to slides using a Fluorsave® Mounting solution (Calbiochem, Merck).

9) LIMK1 Kinase Assay

Compounds were tested in a radiometric LIMK1 assay performed in a final volume of 25 µl containing 3 µl of compound or equivalent amount of DMSO as control, 2 µl (1 ng) of N-terminal 6His-tagged recombinant human LIMK1 (Millipore #14-656, in 20 mM MOPS pH=7.0, 1 mM EDTA, 0.01% NP-40, 5% glycerol, 0.1% β-mercaptoethanol, 1 mg·ml$^{-1}$ Bovine Serum Albumin) and a mixture containing 8 µM MOPS pH=7.0, 200 µM EDTA, 70 µM of recombinant GST-cofilin 1, 25 mM Mg(OAc)$_2$, and 360 µM [γ-$^{32}$P]-ATP.

Assays were performed at 30° C. for 10 minutes before termination by the addition of 5 µl of 3% orthophosphoric acid. 25 µL aliquots were then spotted onto P80 filter square (4 cm²). Filters were rinsed three times for 5 minutes by 0.5% orthophosphoric acid at 4° C. and transferred to scintillation vial. Following addition of scintillation cocktail (Ultima Gold, Perkin-Elmer), $^{32}P$ incorporation was measured using a scintillation counter.

10) LIMK1 Inhibition Reversibility Assay

N-terminal 6H s-tagged recombinant human LIMK1 (Millipore #14-656, 62.5 ng) was incubated with 25 µM Compound 1 (or equivalent amount of DMSO) for 10 minutes at 4° C. in a final volume of 100 µL. Size-exclusion chromatography of this mixture was then performed using 1 ml Biospin P-6 column (Biorad, equilibrated in 20 mM MOPS pH=7.0, 1 mM EDTA, 0.01% NP-40, 5% glycerol, 0.1% β-mercaptoethanol, 1 mg·ml$^{-1}$ Bovine Serum Albumin). LIMK1 kinase activity in input and flow-through were then assayed by radiometric LIMK1 kinase assay.

11) Cellular LIMK1 Activity Assay

HeLa cells were treated by compounds (or equivalent amount of DMSO as control) at indicated concentrations and time. Whole cell extracts were prepared using RIPA buffer (50 mM Tris-HCl pH=7.4, 150 mM NaCl, 1% NP-40, 0.5% sodium deoxycholate, 1% SDS, 1 mM EGTA, 1 mM EDTA, 5% glycerol, 1 mM DTT) supplemented with protease inhibitors (Sigma, P8340) and phosphatase inhibitors (Sigma, P5726). About thirty micrograms of proteins were loaded and migrated through a 12% SDS-PAGE. After electro-transfer, the nitrocellulose membrane was saturated with PBS, 0.1% Tween® 20, 5% Bovin Serum Albumin. Amount and phosphorylation status of cofilin were estimated using the polyclonal antibodies anti-cofilin (Cytoskeleton, #ACFLO2) and anti-phosphocofilin (Ser3) (Cell Signaling, #3311). Goat anti-rabbit IgG-HorseRadish Peroxidase conjugated (Biosource, #ALI0404) was used as secondary antibody. Detection was performed using ECL plus western blotting detection system (GE Healthcare).

EXAMPLE 3

Figure 2:
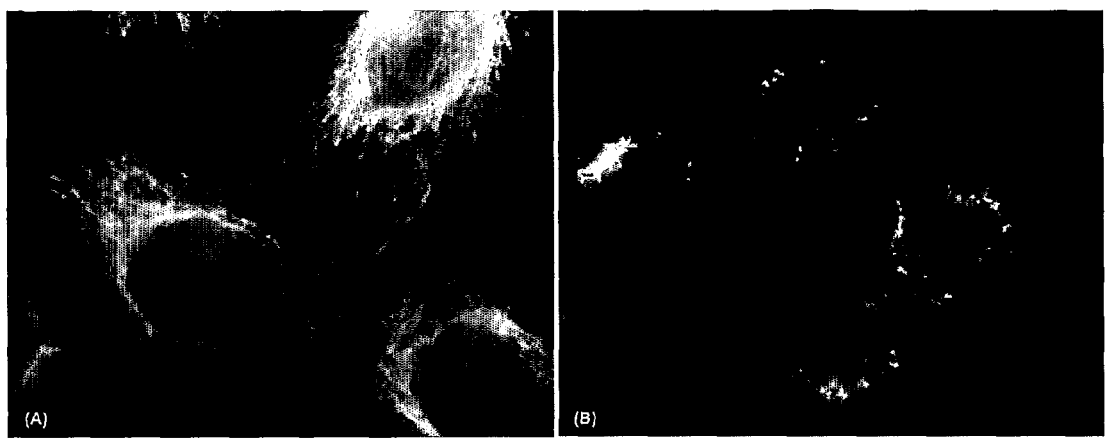

Demonstration of the Stabilizing Properties Of the Compounds of Formula (I) of the Invention In the living cell, microtubules are dynamic structures, which oscillate between assembling and disassembling phases. Various types of tests may be carried out in order to assess the stabilizing effect of the molecules on the microtubule network. Thus, the binding of paclitaxel to the microtubules, or the binding of stabilizing proteins such as STOP proteins (Bosc et al., 2003) may protect the microtubule network from a depolymerization induced by an incubation of the cells at 4° C. Furthermore, molecules capable of slowing down the dynamics of the microtubules may be identified by analyzing the resistance of cell microtubules to a depolymerization induced by nocodazole. In the absence of a stabilizing compound, the microtubules depolymerize in the presence of nocodazole (FIG. 2).

Figure 3:
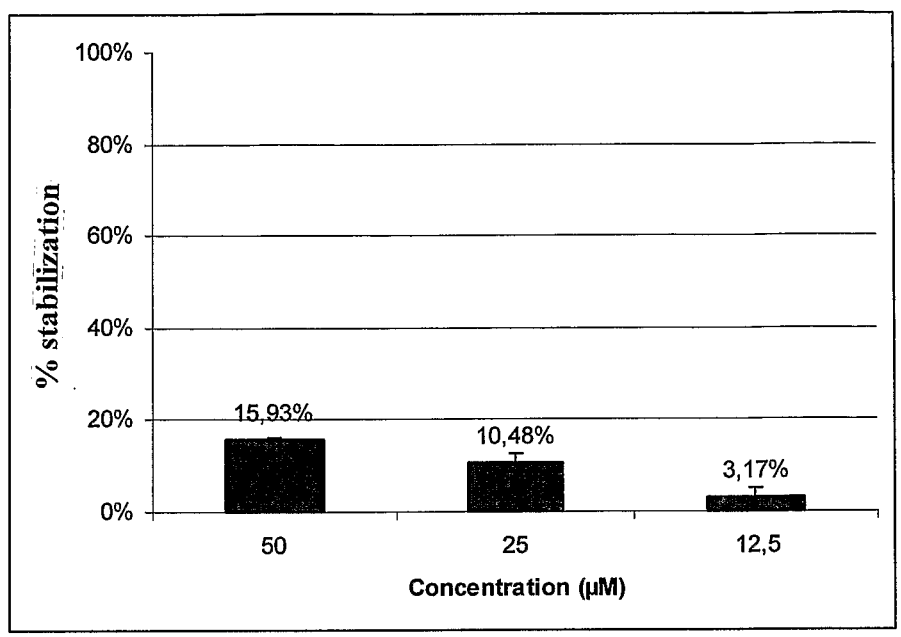
Figure 4:
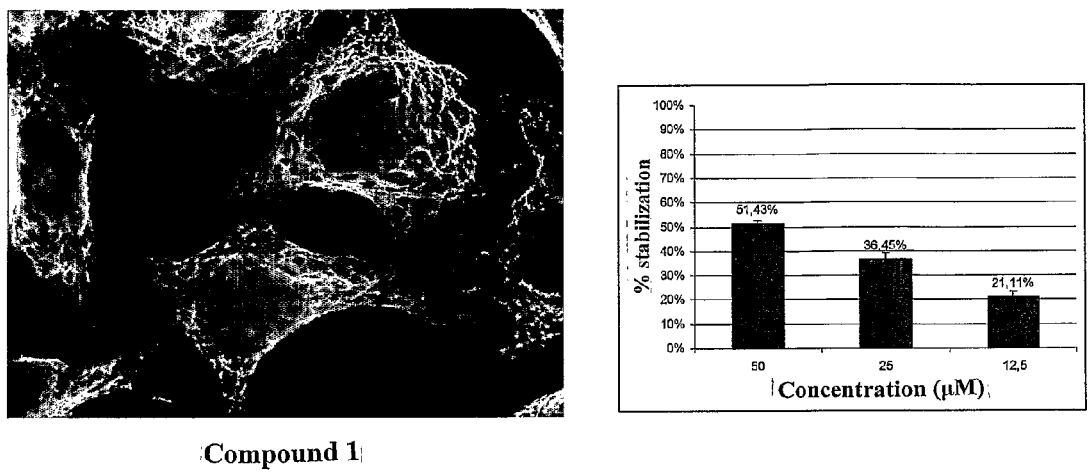

The stabilizing effect of Compound 1 of the invention on cell microtubules has been compared to that of paclitaxel, using these various tests. These experiments have shown that although this compound is not able to protect the microtubules from a cold-induced depolymerization induced by the cold (FIG. 3), it prevents, in a dose-dependent manner, the nocodazole-induced depolymerization (FIG. 4). This compound is therefore capable of slowing down the dynamics of the microtubules.

Table I above summarizes the stabilizing properties of compounds according to the invention, according to qualitative criteria, by double-blind evaluation using a microscope.

EXAMPLE 4

Stabilizing effect of Compound 1 of the Invention by Means of an Effecter

Figure 5:
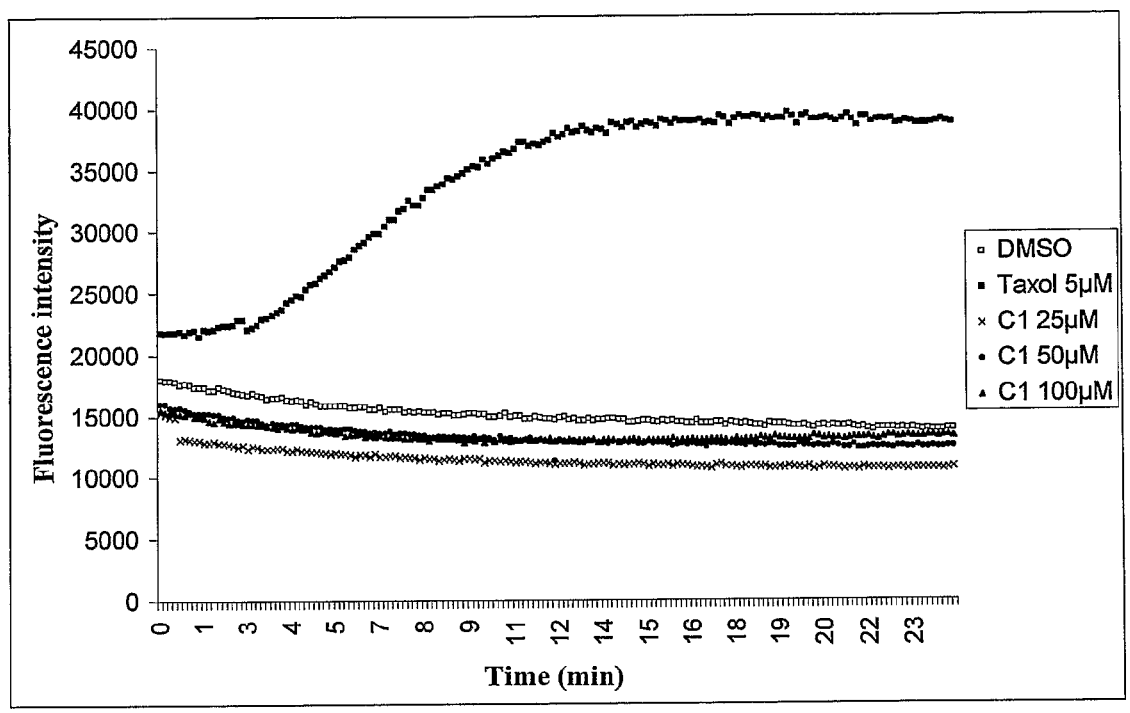

In order to know whether Compound 1 of the invention exerts its stabilizing effect via a direct action on tubulin, such as paclitaxel does, or by means an effector, its effect on the in vitro assembly of tubulin in microtubules has been analyzed. The first experiments were carried out on purified tubulin (1 mg/ml). Only paclitaxel can induce the assembly of tubulin under these conditions. No assembly is observed with Compound 1 of the invention, regardless of the concentration tested (FIG. 5). This result shows that the stabilizing effect of this compound probably does not result from a direct interaction of these molecules with tubulin and that it therefore has an original mode of action.

EXAMPLE 5

Effect of the Compounds According to the Invention on Actin

Figure 6:
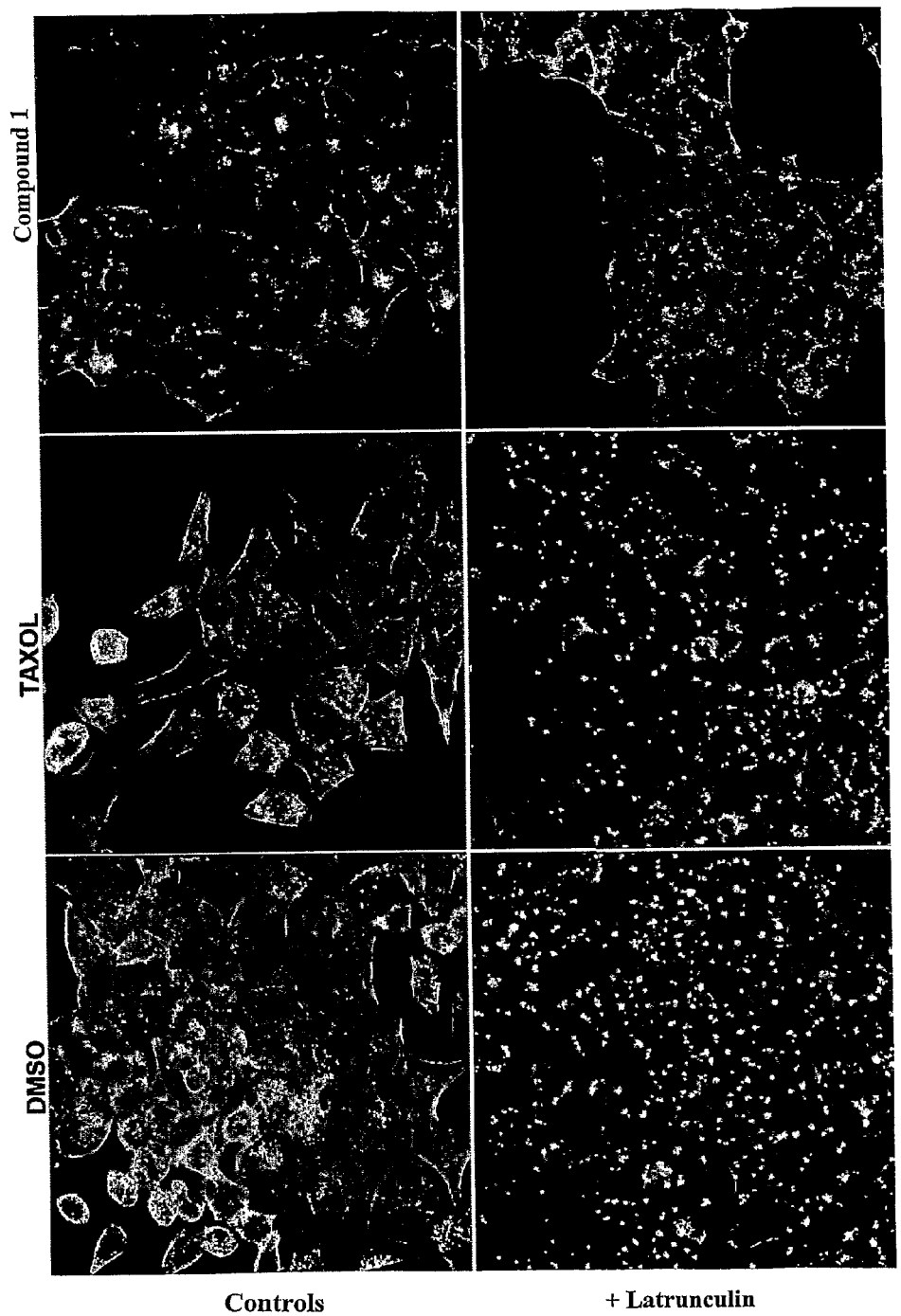
FIG. 6 shows the protective effect of the Compound for a depolymerization induced by latrunculin B on the actin network.

Another effect of the compounds according to the invention is the fact that they are capable of considerably slowing down cell migration. This effect results from an action on the actin cytoskeleton characterized by immunofluorescence experiments as defined in Example 3. However, as for tubulin, the effect of the compounds on the actin cytoskeleton does not result from a direct effect on the polymerization of actin. FIG. 6 illustrates the results obtained with Compound 1 of the invention, which shows that this compound protects the actin network from a depolymerization by latrunculin B (FIG. 6). Neither DMSO nor paclitaxel (Taxol®) are able to induce such a protective effect.

The observation is done using a confocal microscope.

Under these conditions, in the absence of a stabilization of the actin network (DMSO or paclitaxel (Taxol®)), the latrunculin induces an almost complete depolymerization of the actin network. Compound 1 induces a reorganization of the actin network and partially protects the actin network from a latrunculine β-induced depolymerization.

Figure 8:
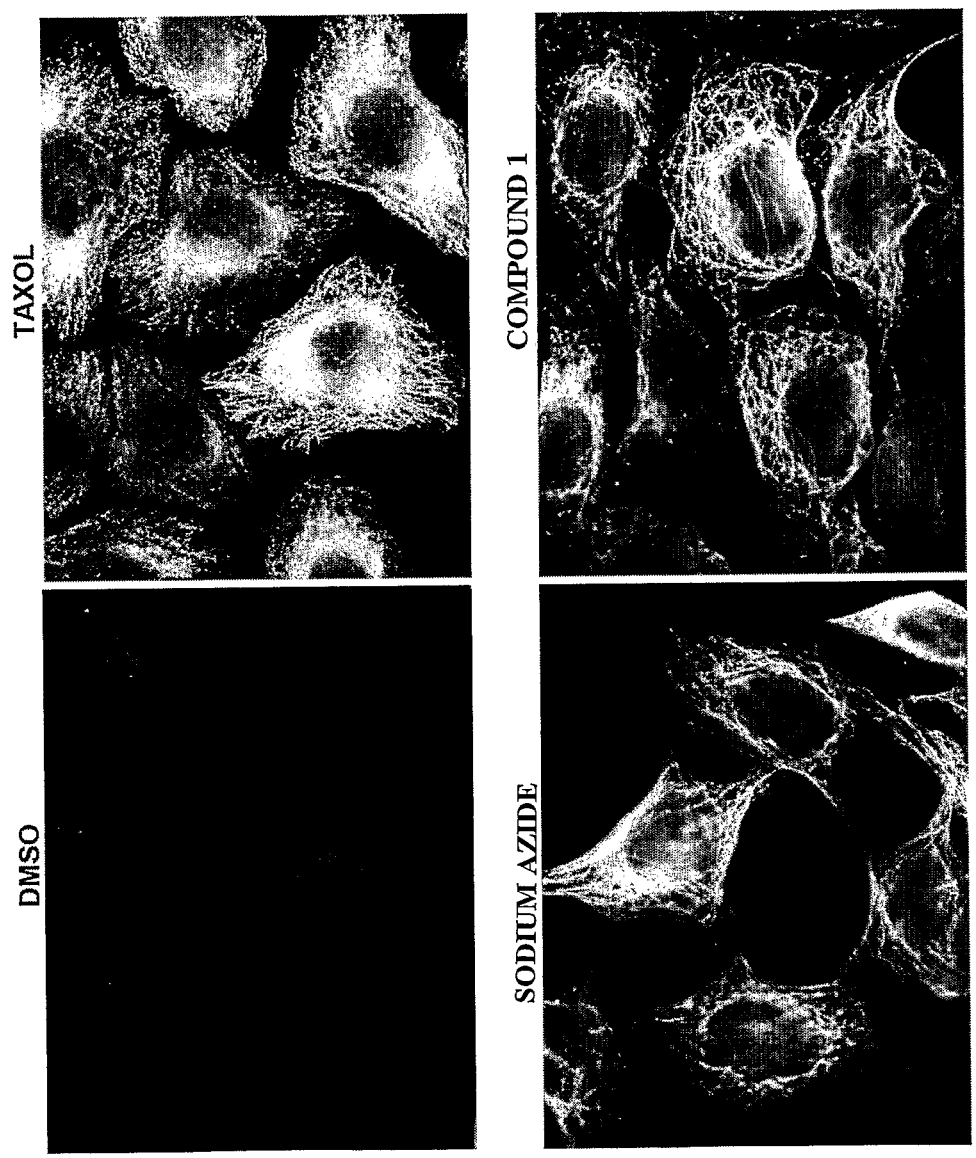
FIG. 8 represents the effect of Compound 1 on the location and morphology of the Glu-microtubules.

Under these conditions, when the microtubule network is stabilized, a very high increase in detyrosinated (with paclitaxel (Taxol®), for example) microtubules is observed compared to the cells treated using DMSO. FIG. 8 illustrates the results obtained.

EXAMPLE 6

Study of the Cytotoxicity with Respect to Cancer Lines

In order to evaluate the effect of these compounds on the growth of cancer lines, the viability of some transformed cell lines, such as HeLa cells (uterine adenocarcinoma), 786-0 cells (renal adeno-carcinoma), NCI-H460 cells (pulmonary carcinoma), MCF-7 cells (breast adenocarcinoma), MES-SA cells (uterine sarcoma) and MES-SA DX5 cells (uterine sarcoma), in the presence of the active compounds, was compared to their viability in the presence of DMSO.

More particularly, the MES-SA DX5 line is a cancer line that expresses a high level of P-glycoprotein and that therefore is resistant to the toxicity induced by the treatment with numerous pharmacological agents. P-glycoprotein was identified as one of the major causes of resistance to chemotherapy of cancers. It is encoded by a gene known as MDR1 (for "multidrug resistance"). Its normal function is to discharge out of the cells the foreign substances and toxins from our environment. The medicaments concerned are anthracyclines, epipodophyllotoxins, Vinca alkaloids, paclitaxel (Taxol®), some intercalating agents such as mitoxantrone and dactinomycin, and certain derivatives of camptothecin.

Figure 7:
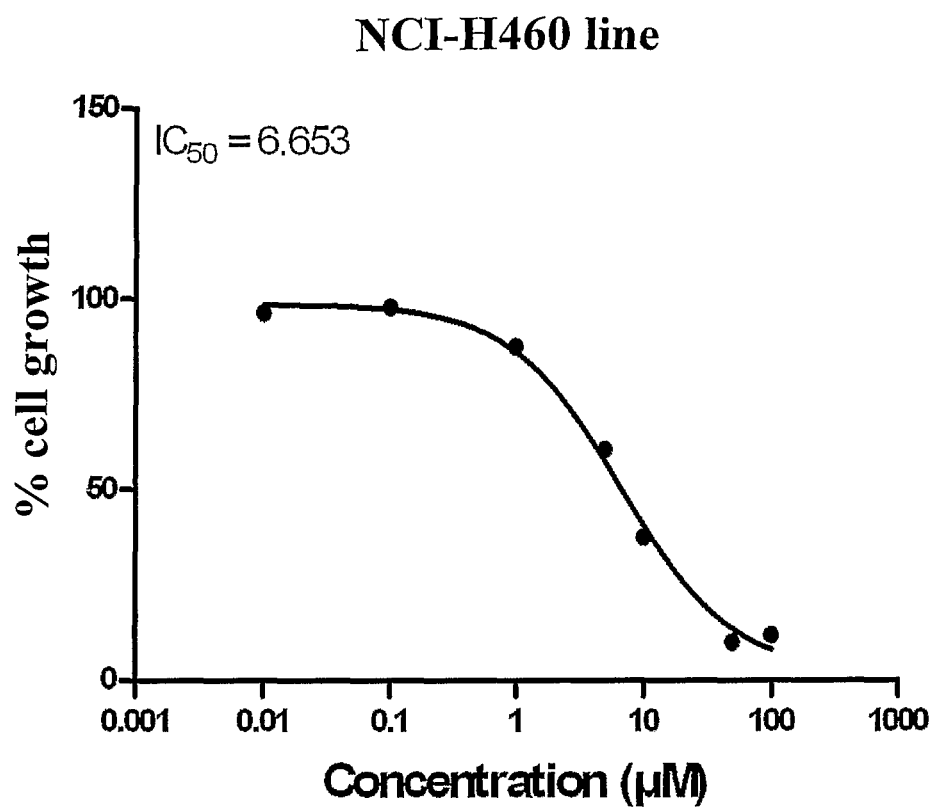
FIG. 7 shows the toxicity of Compound 1 of the invention to NCI-H460 cells. The cells were treated with various concentrations of Compound 1 of the invention for 48 h and the cell viability was measured using the MTT test.

The viability of the cells was evaluated using an MTT test after 48 h of exposure with various concentrations of molecules (from 100 µM to 0.001 µM). Dose-effect curves were thus obtained, which made it possible to determine the concentration necessary to inhibit 50% of cell growth ($IC_{50}$). An example of a cytotoxicity curve is illustrated in FIG. 7.

The effect of Compounds 1 and 3 of the invention on the various cell lines was analyzed. The values of the $IC_{50}$ obtained are presented in Table V below:

TABLE V $IC_{50}$ of Compounds 1 and 3 of the invention on various cancer lines

|  | Compound 1 | Compound 3 |
| --- | --- | --- |
| HeLa | 1.21 µM | 3.05 µM |
| 786-O | 55.09 µM | 3.34 µM |
| NCI-H460 | 6.65 µM | 1.52 µM |
| MCF-7 | 62.20 µM | ND |
| MES-SA | 26.04 µM | 33.90 µM |
| MES-SA DX5 | 27.41 µM | 13.92 µM |

The toxicity of the molecules varies depending of the cell lines. The MCF-7 cells appear to be the most resistant line. For this cell line, the $IC_{50}$ of Compound 3 of the invention, difficult to dissolve at high concentrations, has not been able to be determined. The MES-SA DX5 multi-drug resistant line is, however, sensitive to both molecules.

Finally, Compound 3 of the invention is more toxic than Compound 1 of the invention with respect to the 786-O, NCI-H460 and MES-SA DX5 lines.

EXAMPLE 7

Effect on the Mitochondria

Figure 9:
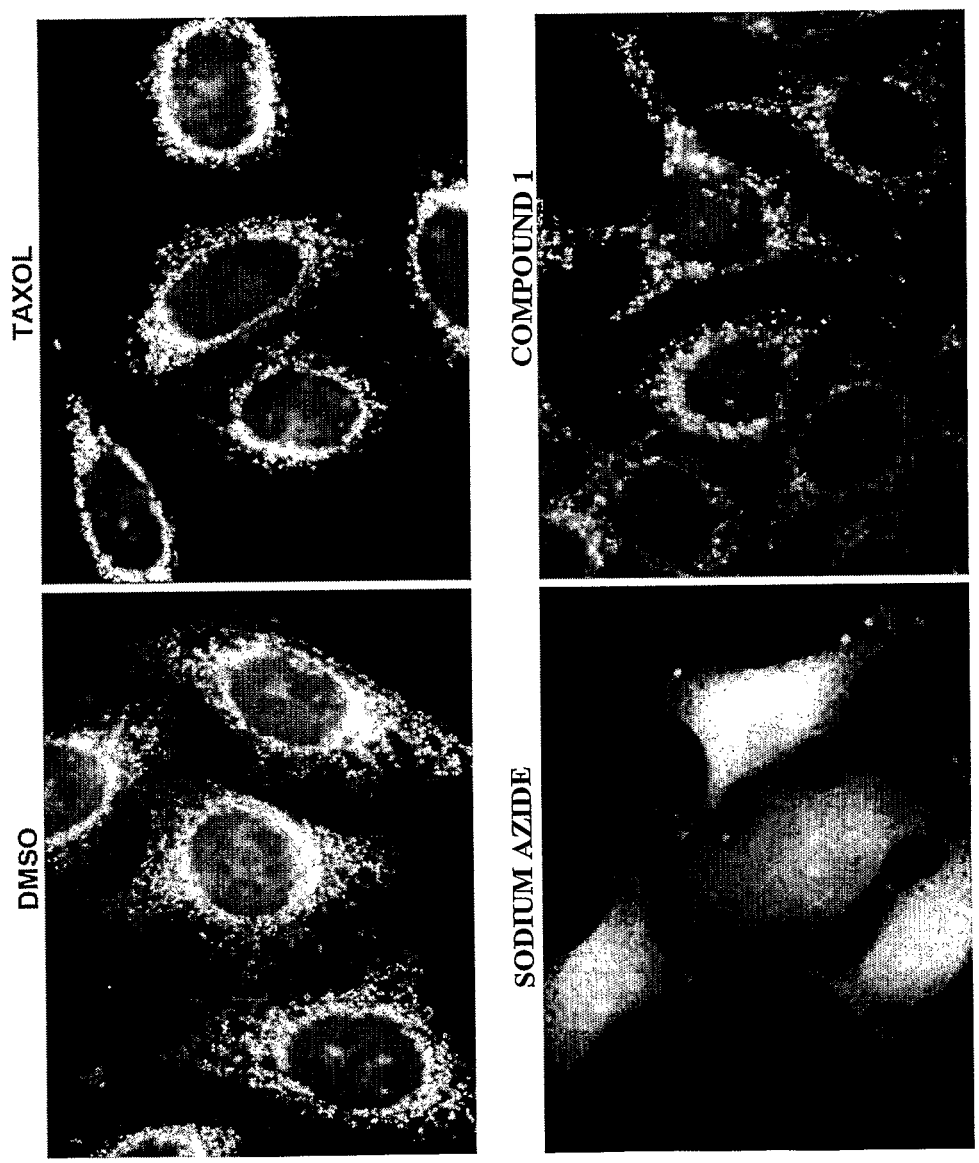
FIG. 9 represents the effect of Compound 1 on the location and morphology of the mitochondria.

After 2 h of treatment at 25 µM (see Examples 2 to 4), Compound 1 does not induce the mitochondrial phenotype observed when cells are treated with sodium azide type (FIG. 9).

EXAMPLE 8

Determination of the $EC_{50}$

For the purpose of evaluating the bioactivity of the molecules in vivo and of comparing their activities, the $EC_{50}$ of the chosen molecules (effective concentration at 50% of the total effect) was determined. Dose-effect curves, which make it possible to measure the variation of the Tyr-tubulin or Glu-tubulin signal in the cells as a function of the concentration of the molecules, were established. It is then possible to define, using these curves, the concentration of bioactive molecule that produces an activity corresponding to 50% of the total effect sought.

A dose-effect curve measuring the variation of the amount of Glu-tubulin was produced for Compound 1 of the invention. For this, HeLa cells were incubated for 2 h with various concentrations of molecules, then treated according to the immunofluorescence protocol in microplates. The fluorescence intensity was then measured using the microplate reader.

The percentage of the signal measured represents its distance relative to the control of bioactivity (paclitaxel (Taxol®)) and to the control of bioinactivity (DMSO). The $EC_{50}$ was determined using KaleidaGraph® 3.60 software.

Compound 1 of the invention is capable, at the highest concentrations, of causing an increase in the Glu signal slightly smaller than that of paclitaxel (Taxol®).

EXAMPLE 9

Inhibition of LIMK1 by Compound 1 In Vitro

Figure 10:
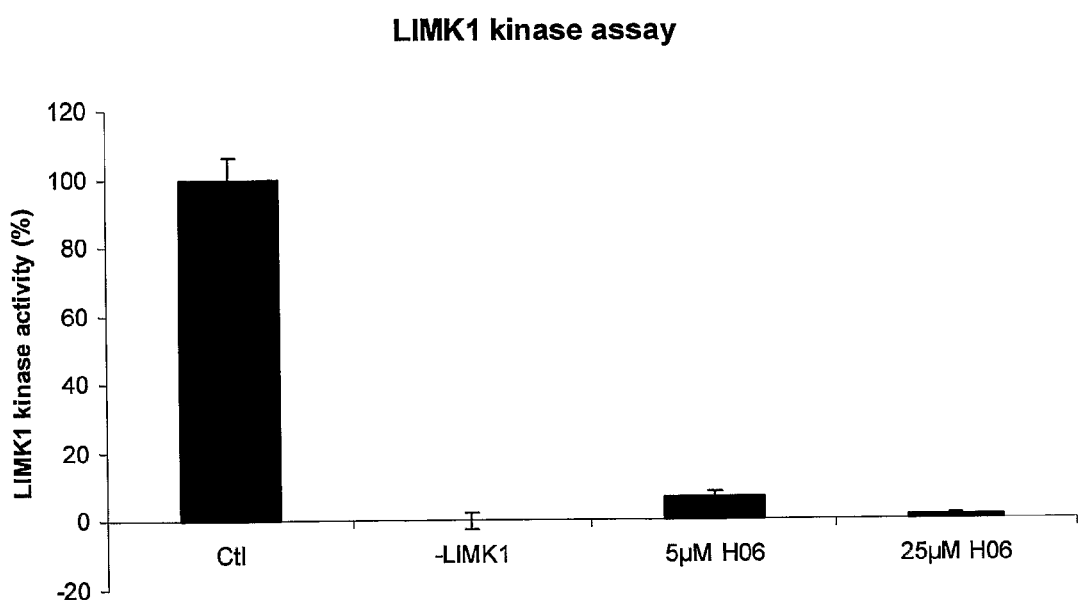
FIG. 10 represents the inhibition of LIMK1 by Compound 1.

FIG. 10 illustrates the inhibition of LIMK1 by Compound 1 (H06). Radiometric LIMK1 kinase assay was performed as described in Example 2; the following conditions were tested: without LIMK1 ('−LIMK1'), with LIMK1 (1 ng) in presence of 5 µM H06 ('5 µM H06'), 25 µM H06 ('25 µM H06') or with equivalent amount of DMSO ('Ctl').

Figure 11:
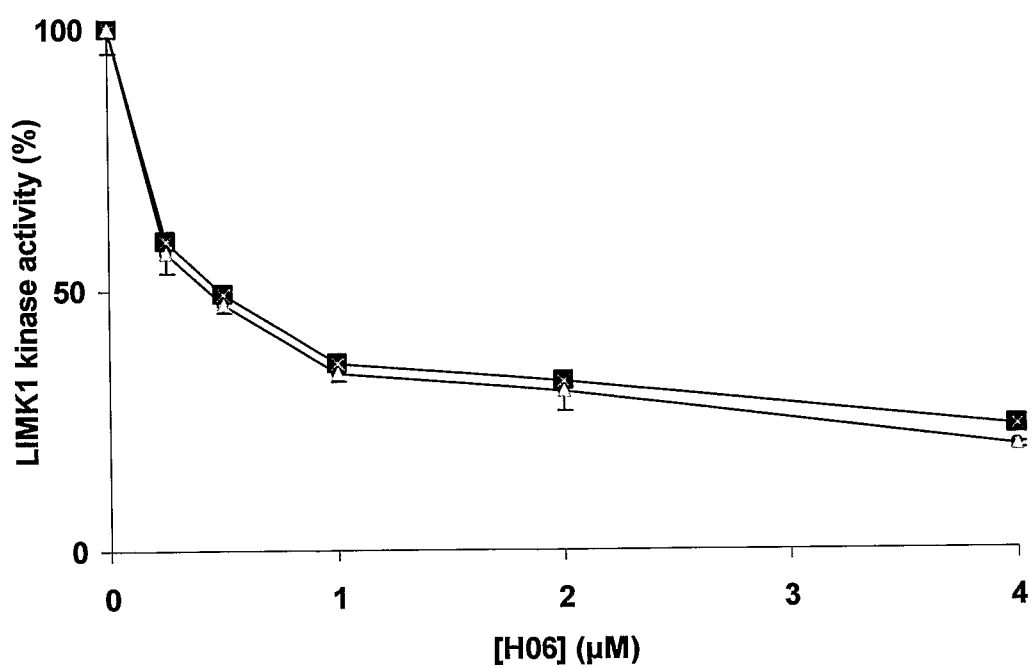
FIG. 11 illustrates the dose-dependent inhibition of LIMK1 by Compound 1.

Said inhibition is dose-dependent as illustrated in FIG. 11, under different ATP concentrations: 180 µM (open circles) or 360 µM (black squares). Error bars represent standard error mean.

Figure 12:
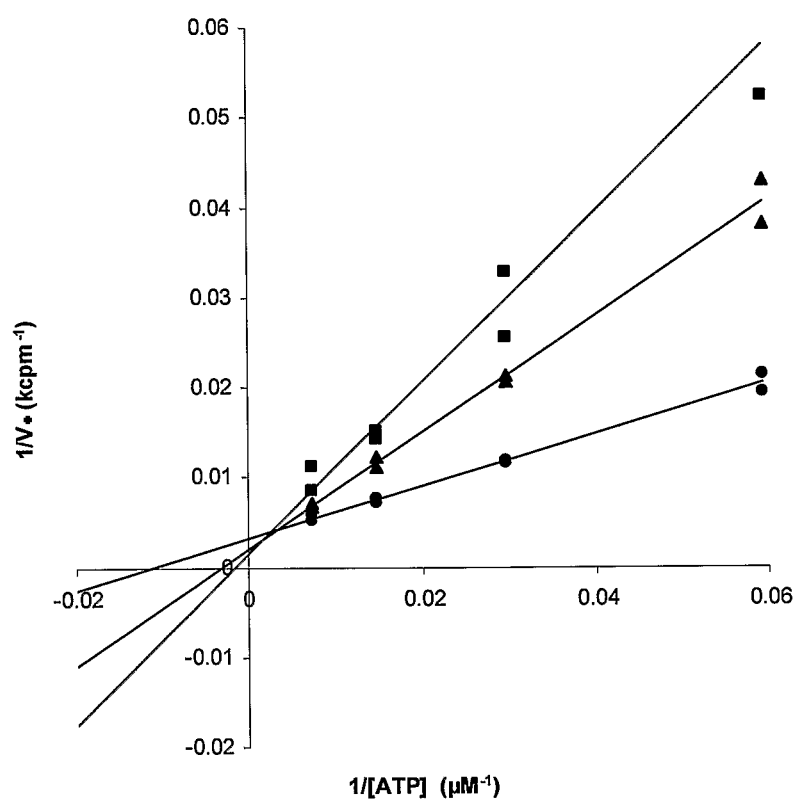
FIG. 12 illustrates Lineweaver-Burk inhibition plots of LIMK1 by Compound 1.

Inhibition mechanism was illustrated in FIG. 12 representing Lineweaver-Burk plots of LIMK1, by determining LIMK1 kinase activity in the absence (●) or in the presence of 70 nM (Δ) and 280 nM (■) of Compound 1 (H06). $V_0$ is the initial GST-cofilin phosphorylation reaction velocity; the results show that Compound 1 is an ATP competitor on LIMK1: $K_i$ of about 60 nM, the $K_m$(ATP) being of about 90 µM.

Figure 13:
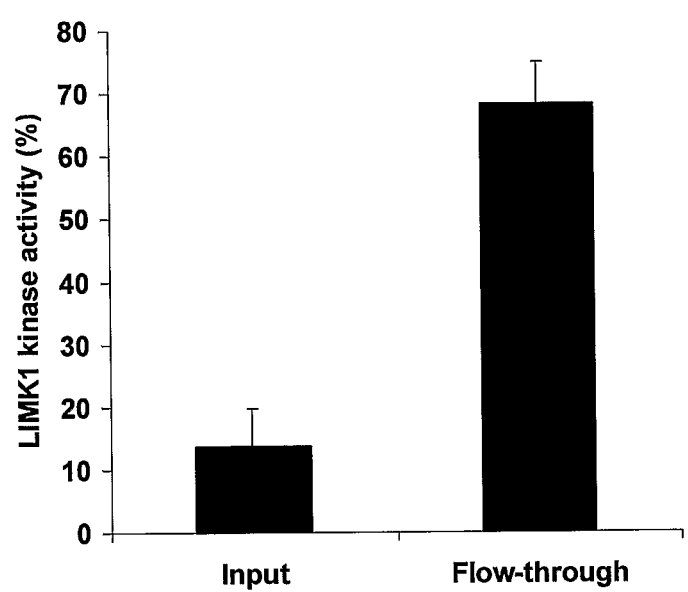
FIG. 13 illustrates the in vitro reversibility of LIMK1 inhibition by Compound 1.

LIMK1 inhibition reversibility was assayed in vitro, in the conditions of Example 2, in the presence of 2 µM Compound 1 (H06), prior ('input') or after size-exclusion chromatography ('flow-through'). Error bars represent standard error mean. FIG. 13 illustrates the results and shows that the action of Compound 1 is reversible.

Analysis of the reversibility of inhibition of Compound 1 was also tested in vivo.

HeLa cells were treated by 25 µM Compound 1 (H06) for 2 h (lane 2). Culture medium was then discarded and fresh medium (RPMI) was added. At different times after RPMI addition (lane 3, 30 minutes; lane 4, 1 hour; lane 5, 1.5 hour; lane 6, 2 hours; lane 7, 4 hours), amount and phosphorylation status of cofilin were determined as described in Example 2. The lane 1 corresponds to time "0", i.e. a cell extract of cells that have not been treated with Compound 1.

Figure 14:
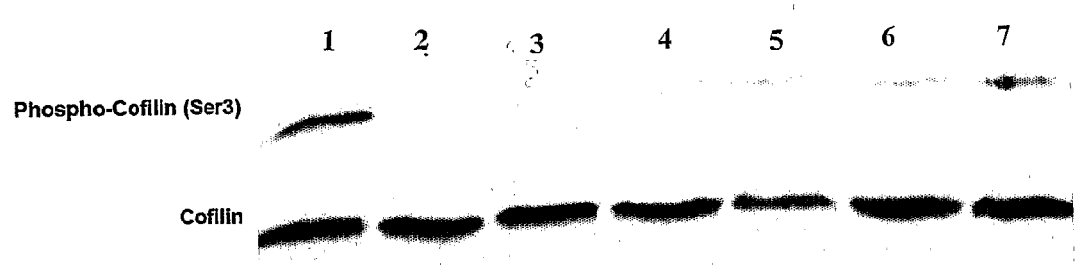
FIG. 14 represents the analysis of the reversibility of inhibition of Ser3-cofilin phosphorylation induced by Compound 1, in HeLa cells.

FIG. 14 illustrates the results and clearly shows that when Compound 1 is replaced by RPMI medium, phospho-cofilin is synthesized again (see lane 4 in FIG. 14).

EXAMPLE 10

In Vivo Inhibition of Cellular LIMK1 Activity by Compound 1

Cofilin is a substrate of LIMK1. Compound 1 induces a dose-dependent Ser3-Cofilin phosphorylation inhibition in HeLa cells.

HeLa cells were treated by indicated concentrations of Compound 1 (or ellipticine as negative control) for 2 h.

Amount and phosphorylation status of cofilin were determined as described in Example 2. In vitro phosphorylated cofilin (left) was used as control.

Figure 15:
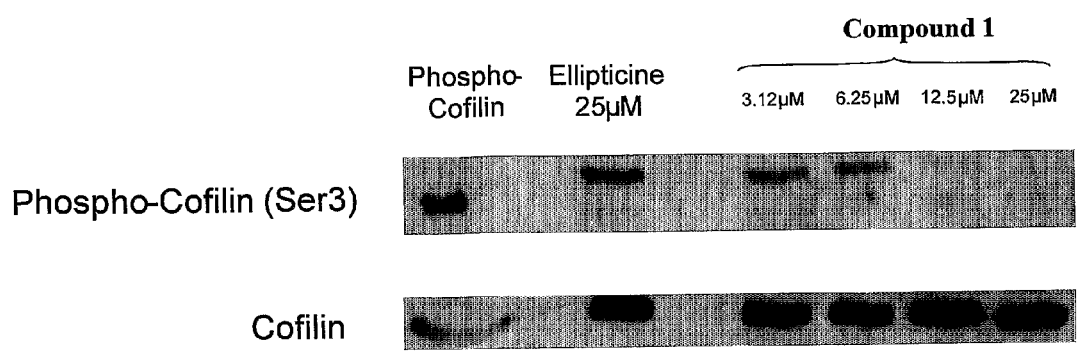
FIG. 15 illustrates the dose-dependent inhibition of cellular LIMK1 activity by Compound 1.

The results (FIG. 15) show that ellipticine does not avoid the phosphorylation of cofilin, whereas Compound 1 clearly inhibits the formation of phospho-cofilin, in a dose-dependent manner, by inhibiting LIMK1.

HeLa cells were treated by 25 µM of Compound 1 for indicated time. Amount and phosphorylation status of cofilin were determined as described in Example 2.

Figure 16:
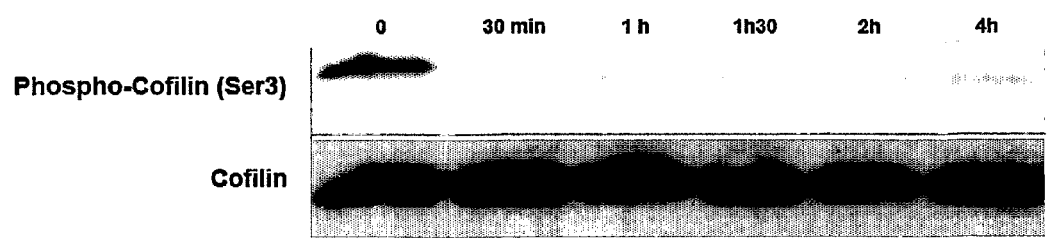
FIG. 16 illustrates the kinetic analysis of Compound 1 inhibition of ser3-cofilin phosphorylation in HeLa cells.

FIG. 16 illustrates this experiment. It shows that the inhibitory effect of Compound 1 can be easily detected after only 30 minutes of treatment with Compound 1.

EXAMPLE 11

Comparative Study Between Compounds of Formula I Wherein R6 Represents an Oxygen Atom Bound to the Ring D by a Double-Bond of the Instant Invention and Compounds with an Amine Derivative Group as $R_6$

| Compounds | $R_6$ | Inhibition of LIMK1 |
|---|---|---|
| Compound 1 (H06) of the invention (5 µM) | =O | + |
| Compound 2 of the invention (5 µM) | =O | + |
| Compound 3 of the invention (5 µM) | =O | + |
| Compound 4 of the invention (5 µM) | =O | + |
| Compound C6 | —NH—(CH$_3$)$_3$—N(CH$_3$)$_2$ | − |
| Compound C8 | —NH—(CH$_3$)$_3$—N(CH$_3$)$_2$ | − |

These comparative data show the crucial role of the selection of $R_6$ according to the invention.

Indeed, in the case where $R_6$ is not as defined in the instant invention, and preferably an oxygen atom bound to the ring D by a double bond, the inhibitory action on LIMK1 is not found.

Figure 17:
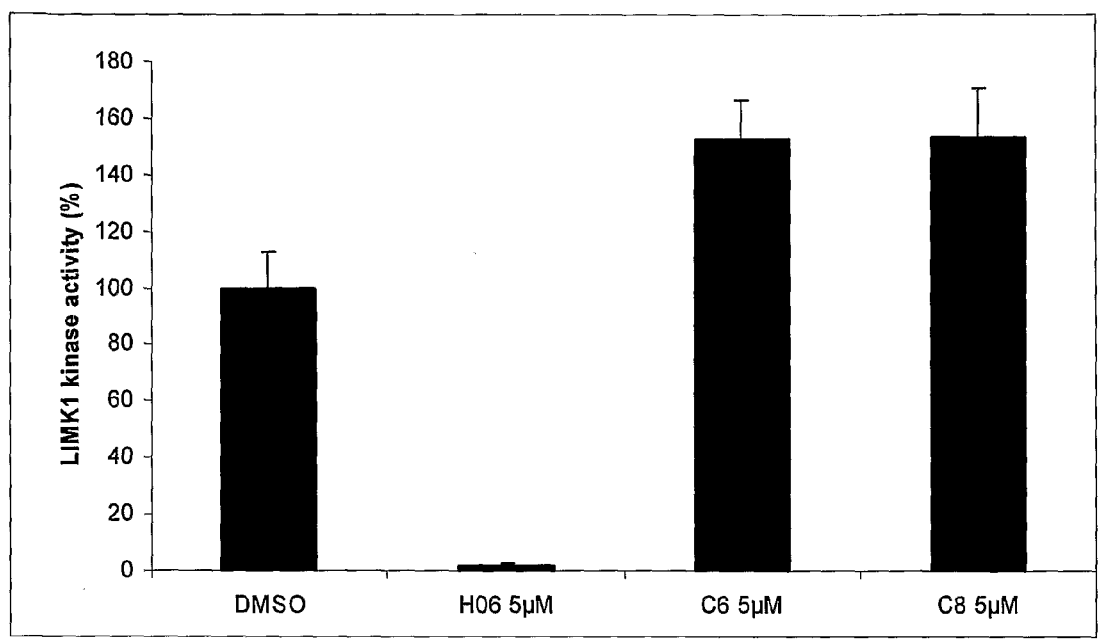
FIG. 17 illustrates the comparative activity on LIMK1 of Compound 1 (H06) of the invention compared to compounds C6 and C8 of the prior art.

FIG. 17 illustrates some of these results.

BIBLIOGRAPHIC REFERENCES

Acevedo, K., R. Li, P. Soo, R. Suryadinata, B. Sarcevic, V. A. Valova, M. E. Graham, P. J. Robinson, and O. Bernard. 2007. The phosphorylation of p25/TPPP by LIM kinase 1 inhibits its ability to assemble microtubules. *Exp Cell Res.* 313:4091-106.

Andrieux, A., P. Salin, A. Schweitzer, M. Begou, B. Pachoud, P. Brun, S. Gory-Faure, P. Kujala, M. F. Suaud-Chagny, G. Hofle, and D. Job. 2006. Microtubule stabilizer ameliorates synaptic function and behavior in a mouse model for schizophrenia. *Biol Psychiatry.* 60:1224-30.

Andrieux, A., P. A. Salin, M. Vernet, P. Kujala, J. Baratier, S. Gory-Faure, C. Bosc, H. Pointu, D. Proietto, A. Schweitzer, E. Denarier, J. Klumperman, and D. Job. 2002. The suppression of brain cold-stable microtubules in mice induces synaptic defects associated with neuroleptic-sensitive behavioral disorders. *Genes Dev.* 16:2350-64.

Arber, S., F. A. Barbayannis, H. Hanser, C. Schneider, C. A. Stanyon, O. Bernard, and P. Caroni. 1998. Regulation of actin dynamics through phosphorylation of cofilin by LIM-kinase. *Nature.* 393:805-9.

Barra, H. S., C. A. Arce, and C. E. Argarana. 1988. Posttranslational tyrosination/detyrosination of tubulin. *Mol. Neurobiol.* 2:133-53.

Baudoin, J. P., C. Alvarez, P. Gaspar, and C. Metin. 2008. Nocodazole-induced changes in microtubule dynamics impair the morphology and directionality of migrating medial ganglionic eminence cells. *Dev Neurosci.* 30:132-43.

Begou, M., J. Voile, J. B. Bertrand, P. Brun, D. Job, A. Schweitzer, M. Saoud, T. D'Amato, A. Andrieux, and M. F. Suaud-Chagny. 2008. The stop null mice model for schizophrenia displays [corrected] cognitive and social deficits partly alleviated by neuroleptics. *Neuroscience.* 157:29-39.

Bernard, O. 2007. Lim kinases, regulators of actin dynamics. *Int J Biochem Cell Biol.* 39:1071-6.

Bhat, K. M., and V. Setaluri. 2007. Microtubule-associated proteins as targets in cancer chemotherapy. *Clin Cancer Res.* 13:2849-54.

Castillo, A., H. C. Morse, 3rd, V. L. Godfrey, R. Naeem, and M. J. Justice. 2007. Overexpression of Eg5 causes genomic instability and tumor formation in mice. *Cancer Res.* 67:10138-47.

De Brabander, M., G. Geuens, R. Nuydens, R. Willebrords, and J. De Mey. 1982. Microtubule stability and assembly in living cells: the influence of metabolic inhibitors, Taxol and pH. *Cold Spring Harb Symp Quant Biol.* 46 Pt 1:227-40.

Dermaut, B., S. Kumar-Singh, R. Rademakers, J. Theuns, M. Cruts, and C. Van Broeckhoven. 2005. Tau is central in the genetic Alzheimer-frontotemporal dementia spectrum. *Trends Genet.* 21:664-72.

Dodion, P., M. Rozencweig, C. Nicaise, M. Piccart, E. Cumps, N. Crespeigne, D. Kisner, and Y. Kenis. 1982. Phase I clinical study of 9-hydroxy-2N-methyl-ellipticinium acetate (NSC-264137) administered on a 5-day i.v. schedule. *Eur J Cancer Clin Oncol.* 18:519-22.

Enomoto, T. 1996. Microtubule disruption induces the formation of actin stress fibers and focal adhesions in cultured cells: possible involvement of the rho signal cascade. *Cell Struct Funct.* 21:317-26.

Fonrose, X., F. Ausseil, E. Soleilhac, V. Masson, B. David, I. Pouny, J. C. Cintrat, B. Rousseau, C. Barette, G. Massiot, and L. Lafanechére. 2007. Parthenolide inhibits tubulin carboxypeptidase activity. *Cancer Res.* 67:3371-8.

Garcia, M. L., and D. W. Cleveland. 2001. Going new places using an old MAP: tau, microtubules and human neurodegenerative disease. *Curr Opin Cell Biol.* 13:41-8.

Giannakakou, P., D. Sackett, and T. Fojo. 2000. Tubulin/microtubules: still a promising target for new chemotherapeutic agents. *J Natl Cancer Inst.* 92:182-3.

Gigant, B., C. Wang, R. B. Ravelli, F. Roussi, M. O. Steinmetz, P. A. Curmi, A. Sobel, and M. Knossow. 2005. Structural basis for the regulation of tubulin by vinblastine. *Nature.* 435:519-22.

Gorovoy, M., J. Niu, O. Bernard, J. Profirovic, R. Minshall, R. Neamu, and T. Voyno-Yasenetskaya. 2005. LIM kinase 1 coordinates microtubule stability and actin polymerization in human endothelial cells. *J Biol. Chem.* 280:26533-42.

Gundersen, G. G., M. H. Kalnoski, and J. C. Bulinski. 1984. Distinct populations of microtubules: tyrosinated and non-tyrosinated alpha tubulin are distributed differently in vivo. *Cell.* 38:779-89.

Gundersen, G. G., S. Khawaja, and J. C. Bulinski. 1987. Postpolymerization detyrosination of alpha-tubulin: a mechanism for subcellular differentiation of microtubules. *J. Cell Biol.* 105:251-64.

Hayat, M., G. Mathe, M. M. Janot, P. Potier, N. Dat-Xuong, A. Cave, T. Sevenet, C. Kan-Fan, J. Poisson, J. Miet, J. Le Men, F. Le Goffic, A. Gouyette, A. Ahond, L. K. Dalton, and T. A. Connors. 1974. Experimental screening of 3 forms and 19 derivatives or analogs of ellipticine: oncostatic effect on 1 1210 leukaemia and immunosuppressive effect of 4 of them. *Biomedicine.* 21:101-6.

Heredia, L., P. Helguera, S. de Olmos, G. Kedikian, F. Sola Vigo, F. LaFerla, M. Staufenbiel, J. de Olmos, J. Busciglio, A. Caceres, and A. Lorenzo. 2006. Phosphorylation of actin-depolymerizing factor/cofilin by LIM-kinase mediates amyloid beta-induced degeneration: a potential mechanism of neuronal dystrophy in Alzheimer's disease. *J. Neurosci.* 26:6533-42.

Jackson, J. R., D. R. Patrick, M. M. Dar, and P. S. Huang. 2007. Targeted anti-mitotic therapies: can we improve on tubulin agents? *Nat Rev Cancer.* 7:107-17.

Jordan, M. A., and L. Wilson. 2004. Microtubules as a target for anticancer drugs. *Nat Rev Cancer.* 4:253-65.

Juret, P., Y. Le Talaer, J. E. Couette, and T. Delozier. 1980. Hydroxy-9-methyl-2-Ellipticinium (NSC 264-137) in 52 cases of osseous metastases from breast cancer. *Eur J Cancer.* Suppl 1:277-9.

Kops, G. J., B. A. Weaver, and D. W. Cleveland. 2005. On the road to cancer: aneuploidy and the mitotic checkpoint. *Nat Rev Cancer.* 5:773-85.

Lafanechére, L. 2008. Chemogenomics and cancer chemotherapy: cell-based assays to screen for small molecules that impair microtubule dynamics. *Comb Chem High Throughput Screen.* 11:617-23.

Lafanechére, L., and D. Job. 2000. The third tubulin pool. *Neurochem Res.* 25:11-8.

Le Mee, S., A. Pierre, J. Markovits, G. Atassi, A. Jacquemin-Sablon, and J. M. Saucier. 1998. S16020-2, a new highly cytotoxic antitumor olivacine derivative: DNA interaction and DNA topoisomerase II inhibition. *Mol. Pharmacol.* 53:213-20.

MacRae, T. H. 1997. Tubulin post-translational modifications—enzymes and their mechanisms of action. *Eur J. Biochem.* 244:265-78.

Margalit, D. N., L. Romberg, R. B. Mets, A. M. Hebert, T. J. Mitchison, M. W. Kirschner, and D. RayChaudhuri. 2004. Targeting cell division: small-molecule inhibitors of FtsZ GTPase perturb cytokinetic ring assembly and induce bacterial lethality. *Proc Natl Acad Sci USA.* 101:11821-6.

Mogilner, A., and K. Keren. 2009. The shape of motile cells. *Curr Biol.* 19:R762-71.

Morrissette, N. S., and L. D. Sibley. 2002. Disruption of microtubules uncouples budding and nuclear division in Toxoplasma gondii. *J Cell Sci.* 115:1017-25.

Muller, C., D. Gross, V. Sarli, M. Gartner, A. Giannis, G. Bernhardt, and A. Buschauer. 2007. Inhibitors of kinesin Eg5: antiproliferative activity of monastrol analogues against human glioblastoma cells. *Cancer Chemother Pharmacol.* 59:157-64.

Niethammer, P., I. Kronja, S. Kandels-Lewis, S. Rybina, P. Bastiaens, and E. Karsenti. 2007. Discrete states of a protein interaction network govern interphase and mitotic microtubule dynamics. *PLoS Biol.* 5:e29.

Pan, J., and W. Snell. 2007. The primary cilium: keeper of the key to cell division. *Cell.* 129:1255-7.

Paoletti, C., J. B. Le Pecq, N. Dat-Xuong, P. Juret, H. Garnier, J. L. Amiel, and J. Rouesse. 1980. Antitumor activity, pharmacology, and toxicity of ellipticines, ellipticinium, and 9-hydroxy derivatives: preliminary clinical trials of 2-methyl-9-hydroxy ellipticinium (NSC 264-137). *Recent Results Cancer Res.* 74:107-23.

Paris, L., M. Thery, J. Faure, Y. Saoudi, L. Lafanechére, J. K. Chilton, P. Gordon-Weeks, N. Galjart, M. Bornens, L. Wordeman, J. Wehland, A. Andrieux, and D. Job. 2006. Tubulin tyrosination is a major factor affecting the recruitment of CAP-Gly proteins at microtubule plus ends. *J Cell Biol.* 174:839-49.

Peris, L., M. Wagenbach, L. Lafanechere, J. Brocard, A. T. Moore, F. Kozielski, D. Job, L. Wordeman, and A. Andrieux. 2009. Motor-dependent microtubule disassembly driven by tubulin tyrosination. *J Cell Biol.* 185:1159-66.

Pugacheva, E. N., S. A. Jablonski, T. R. Hartman, E. P. Henske, and E. A. Golemis. 2007. HEF1-dependent Aurora A activation induces disassembly of the primary cilium. *Cell.* 129:1351-63.

Ruthel, G., G. L. Demmin, G. Kallstrom, M. P. Javid, S. S. Badie, A. B. Will, T. Nelle, R. Schokman, T. L. Nguyen, J. H. Carra, S. Bavari, and M. J. Aman. 2005. Association of ebola virus matrix protein VP40 with microtubules. *J Virol.* 79:4709-19.

Scott, R. W., and M. F. Olson. 2007. LIM kinases: function, regulation and association with human disease. *J Mol Med.* 85:555-68.

Snyder, J. P., J. H. Nettles, B. Cornett, K. H. Downing, and E. Nogales. 2001. The binding conformation of Taxol in beta-tubulin: a model based on electron crystallographic density. *Proc Natl Acad Sci U S A.* 98:5312-6.

Tura, S., F. Mandelli, P. Mazza, G. Cimino, A. P. Anselmo, and S. Amadori. 1984. 2-Methyl-9-hydroxyellipticinium acetate (ellipticinium) in the treatment of lymphomas. Preliminary results of a phase II study. *Chemioterapia.* 3:79-82.

Vassal, E., C. Barette, X. Fonrose, R. Dupont, E. Sans-Soleilhac, and L. Lafanechére. 2006. Miniaturization and validation of a sensitive multiparametric cell-based assay for the concomitant detection of microtubule-destabilizing and microtubule-stabilizing agents. *J Biomol Screen.* 11:377-89.

Wang, W., R. Eddy, and J. Condeelis. 2007. The cofilin pathway in breast cancer invasion and metastasis. *Nat Rev Cancer.* 7:429-40.

Wehland, J., and K. Weber. 1987. Turnover of the carboxy-terminal tyrosine of alpha-tubulin and means of reaching elevated levels of detyrosination in living cells. *J Cell Sci.* 88 Pt 2): 185-203.

Yang, N., O. Higuchi, K. Ohashi, K. Nagata, A. Wada, K. Kangawa, E. Nishida, and K. Mizuno. 1998. Cofilin phosphorylation by LIM-kinase 1 and its role in Rac-mediated actin reorganization. *Nature.* 393:809-12.

Yoshioka, K., V. Foletta, O. Bernard, and K. Itoh. 2003. A role for LIM kinase in cancer invasion. *Proc Natl Acad Sci USA.* 100:7247-52.

Zhou, J., and P. Giannakakou. 2005. Targeting microtubules for cancer chemotherapy. *Curr Med Chem Anticancer Agents.* 5:65-71.

The invention claimed is:

1. A pharmaceutical composition, comprising:

at least one pharmaceutically acceptable vehicle; and at least one tetracyclic compound of formula (I), or a pharmaceutically acceptable salt of the tetracyclic compound:

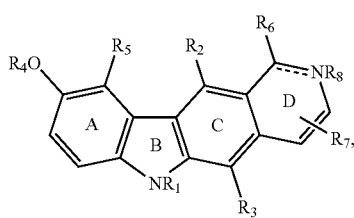

wherein:
R₁ represents a hydrogen atom, an alkyl radical having 1 to 4 carbon atoms, an aminoalkyl group having 1 to 4 carbon atoms, or a monoalkylaminoalkyl, or dialkylaminoalkyl group wherein the two alkyl radicals have 1 to 4 carbon atoms;
R₂ represents a hydrogen atom or an alkyl radical having 1 to 4 carbon atoms;
R₃ represents an alkyl radical having 1 to 4 carbon atoms;
—OR₄ represents a hydroxyl radical, an alkoxy radical having 1 to 4 carbon atoms or an alkoxy radical of formula —O—(CH₂)ₙ—Z, or an ester radical having 1 to 4 carbon atoms, or an ester radical of formula —OC(O)Z, wherein
  Z is a cycloalkyl group having 3 to 6 carbon atoms, or an aryl group, chosen from phenyl, benzyl, pyridyl, pyrimidyl, triazyl, and oxazolyl groups, wherein the aryl group is optionally substituted at the ortho, meta, or para position by one, two, or three substituents, which are identical or different, selected from the group consisting of a halogen atom, —OH, —NO₂, —NH₂, a alkyl radical having 1 to 4 carbon atoms, an alkoxy radical having 1 to 4 carbon atoms, monoalkylamino radical having 1 to 4 carbon atoms, and dialkylamino radical having 1 to 4 carbon atoms, and
  n is an integer ranging from 1 to 4; or
—OR₄ represents a radical of formula:

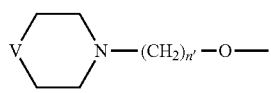

wherein:
  V is selected from the group consisting of CH₂, O, NH, and N-alkyl, wherein the alkyl group has 1 to 4 carbon atoms, and
  n' is equal to 2 or 3;
R₅ represents a hydrogen atom or a dialkylamino-methyl group in which the alkyl radical has 1 to 4 carbon atoms;
R₆ represents an oxygen atom bound to the ring D by a double bond or a halogen atom;
R₇ represents a hydrogen atom or an alkyl radical having 1 to 4 carbon atoms;
R₈ represents a hydrogen atom, an alkyl radical, a hydroxyalkyl radical, an alkylcarboxyalkylene radical of formula

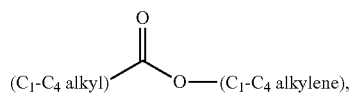

or a dialkylphosphatealkylene radical of formula,

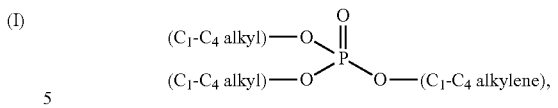

wherein the alkyl and alkylene radicals have 1 to 4 carbon atoms, or an ester radical having 1 to 4 carbon atoms,
with the proviso that R₈ is present only when R₆ is an oxygen atom bound to the D ring by a double bond.

2. The pharmaceutical composition of claim 1, wherein R₁ of formula (I) is a hydrogen atom.

3. The pharmaceutical composition of claim 1, wherein R₂ of formula (I) is a methyl radical.

4. The pharmaceutical composition of claim 1, wherein R₃ of formula (I) is a methyl radical.

5. The pharmaceutical composition of claim 1, wherein the —OR₄ radical of formula (I) is an —OH group or a methoxy radical.

6. The pharmaceutical composition of claim 1, wherein the —OR₄ radical of formula (I) is a benzyl ether radical of formula —O—CH₂—C₆H₅, or an ester radical of formula
  —OC(O)C₆H₅, wherein the ester radical is optionally substituted at at least one of the ortho, meta, and para positions by a substituent selected from the group consisting of —NO₂, —NH₂, —N(CH₃)₂, —CN, —CH₂NH₂, and —CH₂N(CH₃)₂.

7. The pharmaceutical composition of claim 1, wherein R₅ of formula (I) is a hydrogen atom or a dimethylaminomethyl radical.

8. The pharmaceutical composition of claim 1, wherein R₆ of formula (I) is an oxygen atom bound to the ring D by a double bond.

9. The pharmaceutical composition of claim 1, wherein R₈ of formula (I) is a hydrogen atom.

10. The pharmaceutical composition of claim 1, wherein the compound or salt of having a formula (I) is selected from the group of compounds consisting of Compound 1, Compound 3, Compound 4, Compound 9 and Compound 11:

Compound 1

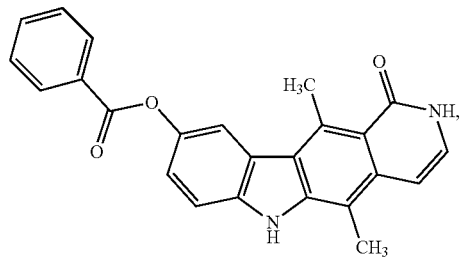

Compound 3

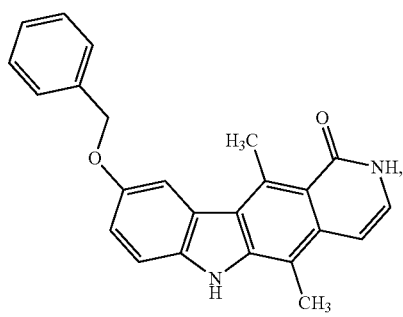

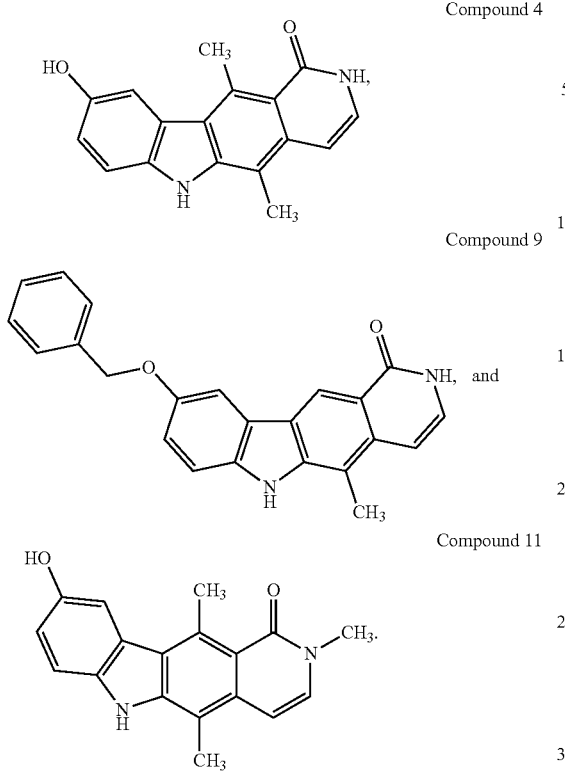

11. A compound of formula:

or a pharmaceutically acceptable salt of compound 10.

12. The pharmaceutical composition of claim 1, further comprising:
another anticancer active principle.

13. A method of evaluating an anticancer activity of a compound or salt of claim 1, the method comprising:
(1) after incubating eukaryotic cells with a compound to be tested, permeabilizing the cells with a buffer which protects a microtubule network of the cells but allows the elimination of the depolymerized tubulin;
(2) after fixation of the cells, labelling the Tyr-tubulin with an anti-tyrosinated tubulin primary antibody and a secondary antibody which emits at a wavelength λ1, labelling the Glu-tubulin with an anti-detyrosinated tubulin primary antibody and a secondary antibody which emits at a wavelength λ2, followed by quantifying fluorescence at various wavelengths, with an aim to identify dynamic microtubules most sensitive to depolymerizing agents and stabilized microtubules;
(3) supplementally labelling nuclei of the cells, in order to evaluate a state of a cell layer of the cells;
(4) incubating the compound to be tested with HeLa cells under the same conditions as (1) and eliminating the compound if a fluorescence is observed at the wavelength λ2;
(5) staining a sample of incubated cells with a mitochondrial marker, and staining a sample of the incubated cells with sodium azide and comparing an effect of the sodium azide, and the compound to be tested, on mitochondria of the cells, and excluding the compound If it exhibits a modification of mitochondria staining similar to that of sodium azide;
(6) incubating HeLa cells with the compound to be tested, optionally treating the HeLa cells with nocodazole, then analyzing an immunofluorescence labelling of the microtubule network and quantifying with a reader; and
(7) incubating the HeLa cells with the compound to be tested, optionally followed by co-incubating with latrunculin B, and labelling of F-actin by a phallotoxin coupled to a fluorophore emitting at λ2, in order to analyze an effect of the test compound to be tested on an actin network of the HeLa cells and to eliminate the compound if it does not modify a morphology of the actin network.

14. An in vitro method for screening at least one molecule susceptible to inhibit or stabilize an activity of LIMK1, the method comprising:
(i) contacting LIMK1 with the compound or salt of claim 1, optionally labelled,
(ii) adding a test compound to be tested, and
(iii) evaluating a displacement of the compound or salt by the test compound.

15. An in vivo method for screening a direct or indirect LIMK1 activator or a phosphatase inhibitor, the method comprising:
(i) contacting the compound or salt of claim 1 with a eukaryotic cell;
(ii) evaluating an inhibitor effect of the compound or salt by measuring a decrease of phosphorylation of a LIMK1 substrate;
(iii) adding a test compound to be tested, and
(iv) measuring an effect of the test compound on an inhibition of the LIMK1 substrate phosphorylation.

16. A method of treating cancer, the method comprising administering to a subject in need therein, an effective amount of a medicine comprising the compound or salt of claim 1.

* * * * *